United States Patent
Clague et al.

(10) Patent No.: US 8,480,696 B2
(45) Date of Patent: Jul. 9, 2013

(54) MINIMALLY INVASIVE CORING VEIN HARVESTER

(75) Inventors: Cynthia T. Clague, Minnetonka, MN (US); Michael J. Hobday, Lino Lakes, MN (US); Raymond W. Usher, Coon Rapids, MN (US); Roderick E. Briscoe, Rogers, MN (US); Katherine S. Jolly, Eden Prairie, MN (US); Ana R. Buhr, Minneapolis, MN (US); Christopher P. Olig, Eden Prairie, MN (US); Eric A. Meyer, Andover, MN (US); Steven C. Christian, New Brighton, MN (US); Tom P. Daigle, Corcoran, MN (US); Robert H. Reetz, Rockford, MN (US); Jeffrey D. Sandstrom, Forest Lake, MN (US); James R. Keogh, Maplewood, MN (US); Matthew D. Bonner, Plymouth, MN (US); Scott E. Jahns, Hudson, WI (US)

(73) Assignee: Medtronic, Inc., Minneapolis, MN (US)

( * ) Notice: Subject to any disclaimer, the term of this patent is extended or adjusted under 35 U.S.C. 154(b) by 1015 days.

(21) Appl. No.: 11/155,533

(22) Filed: Jun. 16, 2005

(65) Prior Publication Data
US 2007/0005084 A1      Jan. 4, 2007

Related U.S. Application Data

(60) Provisional application No. 60/580,237, filed on Jun. 16, 2004.

(51) Int. Cl.
*A61B 17/22*      (2006.01)

(52) U.S. Cl.
USPC .......................................................... 606/159

(58) Field of Classification Search
USPC .................. 606/84, 159, 170, 171, 108, 167, 606/180; 604/22
See application file for complete search history.

(56) References Cited

U.S. PATENT DOCUMENTS

| | | | |
|---|---|---|---|
| 1,867,624 | A | 7/1932 | Hoffman |
| 2,001,169 | A | 5/1935 | Wallace |
| 2,011,169 | A | 8/1935 | Wappler |
| 2,028,635 | A | 1/1936 | Wappler |

(Continued)

FOREIGN PATENT DOCUMENTS

| | | |
|---|---|---|
| DE | 3 942 589 | 7/1991 |
| GB | 2 082 459 | 3/1982 |

(Continued)

OTHER PUBLICATIONS

Gundry, et al., "Optimal preparation techniques for human saphenous vein grafts," Surgery, (1980) 88(6):785-94.

(Continued)

*Primary Examiner* — Thomas McEvoy

(57) ABSTRACT

The invention provides a system and method for harvesting a vessel section. The system comprises a vessel support member, a handle, and a tubular cutting device. The vessel support member is introduced into the vessel section to be harvested. The tubular cutting device may comprise an outer tubular member or an outer and an inner tubular member. The outer tubular member carries at least one cutting element. The tubular member or members are advanced over the vessel section and vessel support member to core out the vessel section and tissue adjoining the vessel section.

8 Claims, 44 Drawing Sheets

U.S. PATENT DOCUMENTS

| | | |
|---|---|---|
| 2,316,297 A | 4/1943 | Southerland et al. |
| 2,868,206 A | 1/1959 | Stoesser |
| 2,944,552 A | 7/1960 | Cannon |
| 3,185,155 A | 5/1965 | Slaten et al. |
| 3,336,916 A | 8/1967 | Edlich |
| 3,856,016 A | 12/1974 | Davis |
| 3,882,854 A | 5/1975 | Hulka et al. |
| 3,934,115 A | 1/1976 | Peterson |
| 4,038,987 A | 8/1977 | Komiya |
| 4,151,838 A | 5/1979 | Crew |
| 4,324,262 A * | 4/1982 | Hall ............... 600/569 |
| 4,362,160 A | 12/1982 | Hiltebrandt |
| 4,369,768 A | 1/1983 | Vukovic |
| 4,440,170 A | 4/1984 | Golden et al. |
| 4,479,497 A * | 10/1984 | Fogarty et al. ........ 606/194 |
| 4,556,058 A | 12/1985 | Green |
| 4,586,919 A | 5/1986 | Taheri |
| 4,638,802 A | 1/1987 | Okada |
| 4,653,476 A | 3/1987 | Bonnet |
| 4,653,496 A * | 3/1987 | Bundy et al. ............ 606/159 |
| 4,729,763 A * | 3/1988 | Henrie ................ 604/22 |
| 4,745,908 A | 5/1988 | Wardle |
| 4,759,348 A | 7/1988 | Cawood |
| 4,759,364 A | 7/1988 | Boebell |
| 4,762,120 A | 8/1988 | Hussein |
| 4,768,508 A | 9/1988 | Chin et al. |
| 4,793,346 A | 12/1988 | Mindich |
| 4,819,634 A * | 4/1989 | Shiber ................ 606/159 |
| 4,821,718 A * | 4/1989 | Uldall ................ 606/159 |
| 4,858,595 A | 8/1989 | Buess et al. |
| 4,862,874 A | 9/1989 | Kellner |
| 4,869,268 A | 9/1989 | Yoon |
| 4,877,016 A | 10/1989 | Kantor et al. |
| 4,909,258 A | 3/1990 | Kuntz et al. |
| 4,932,952 A | 6/1990 | Wojciechowicz, Jr. |
| 4,946,440 A * | 8/1990 | Hall ............... 604/164.09 |
| 4,997,436 A | 3/1991 | Oberlander |
| 5,013,312 A | 5/1991 | Parins et al. |
| 5,020,514 A | 6/1991 | Heckele |
| 5,037,433 A | 8/1991 | Wilk et al. |
| 5,047,038 A | 9/1991 | Peters et al. |
| 5,213,093 A | 5/1993 | Swindle |
| 5,284,478 A | 2/1994 | Nobles et al. |
| 5,290,282 A | 3/1994 | Casscells |
| 5,306,244 A * | 4/1994 | Shiber ................ 604/510 |
| 5,352,222 A | 10/1994 | Rydell |
| 5,373,840 A | 12/1994 | Knighton |
| 5,389,100 A * | 2/1995 | Bacich et al. ........ 606/108 |
| 5,423,806 A * | 6/1995 | Dale et al. ........... 606/15 |
| 5,425,355 A | 6/1995 | Kulick |
| 5,447,513 A | 9/1995 | Davison et al. |
| 5,514,134 A | 5/1996 | Rydell et al. |
| 5,549,637 A | 8/1996 | Crainich |
| 5,593,418 A * | 1/1997 | Mollenauer ........... 606/192 |
| 5,601,581 A | 2/1997 | Fogarty et al. |
| 5,634,935 A * | 6/1997 | Taheri ................ 606/190 |
| 5,651,781 A * | 7/1997 | Grace ................. 606/1 |
| 5,653,722 A | 8/1997 | Kieturakis |
| 5,667,480 A | 9/1997 | Knight et al. |
| 5,695,514 A | 12/1997 | Chin |
| 5,697,946 A | 12/1997 | Hopper et al. |
| 5,722,934 A | 3/1998 | Knight et al. |
| 5,725,479 A | 3/1998 | Knight et al. |
| 5,730,748 A | 3/1998 | Fogarty |
| 5,730,757 A | 3/1998 | Benetti et al. |
| 5,772,576 A | 6/1998 | Knighton et al. |
| 5,797,946 A | 8/1998 | Chin |
| 5,836,945 A | 11/1998 | Perkins |
| 5,853,417 A | 12/1998 | Fogarty et al. |
| RE36,043 E | 1/1999 | Knighton |
| 5,871,496 A | 2/1999 | Ginn et al. |
| 5,876,413 A | 3/1999 | Fogarty et al. |
| 5,891,140 A | 4/1999 | Ginn et al. |
| 5,893,858 A | 4/1999 | Spitz |
| 5,895,353 A | 4/1999 | Lunsford et al. |
| 5,899,913 A | 5/1999 | Fogarty et al. |
| 5,902,315 A | 5/1999 | DuBois |
| 5,913,866 A | 6/1999 | Ginn et al. |
| 5,913,870 A | 6/1999 | DeFonzo et al. |
| 5,916,233 A | 6/1999 | Chin |
| 5,922,004 A | 7/1999 | DuBois |
| 5,928,135 A | 7/1999 | Knight et al. |
| 5,928,138 A | 7/1999 | Knight et al. |
| 5,938,680 A | 8/1999 | Ginn |
| 5,944,736 A | 8/1999 | Taylor et al. |
| 5,967,971 A | 10/1999 | Bolser |
| 5,968,065 A | 10/1999 | Chin |
| 5,968,066 A | 10/1999 | Fogarty et al. |
| 5,970,982 A | 10/1999 | Perkins |
| 5,971,938 A * | 10/1999 | Hart et al. ............. 600/562 |
| 5,976,168 A | 11/1999 | Chin |
| 5,976,171 A | 11/1999 | Taylor |
| 5,980,515 A * | 11/1999 | Tu ................... 606/41 |
| 5,980,549 A | 11/1999 | Chin |
| 5,984,937 A | 11/1999 | Morse et al. |
| 5,993,384 A | 11/1999 | Lunsford et al. |
| 6,019,720 A | 2/2000 | Bito |
| 6,019,771 A | 2/2000 | Bennett et al. |
| 6,022,313 A | 2/2000 | Ginn et al. |
| 6,030,406 A | 2/2000 | Davis et al. |
| 6,036,713 A | 3/2000 | Kieturakis |
| 6,036,714 A | 3/2000 | Chin |
| 6,042,538 A | 3/2000 | Puskas |
| 6,059,802 A | 5/2000 | Ginn |
| 6,068,639 A | 5/2000 | Fogarty et al. |
| 6,071,232 A | 6/2000 | Knighton et al. |
| 6,077,289 A | 6/2000 | Mollenauer |
| 6,110,190 A | 8/2000 | Ginn et al. |
| 6,113,588 A | 9/2000 | Duhaylongsod et al. |
| 6,143,008 A | 11/2000 | Eaves |
| 6,149,584 A | 11/2000 | Raju |
| 6,162,173 A | 12/2000 | Chin et al. |
| 6,176,825 B1 | 1/2001 | Chin et al. |
| 6,193,653 B1 | 2/2001 | Evans |
| 6,196,968 B1 | 3/2001 | Rydin |
| 6,203,557 B1 | 3/2001 | Chin |
| 6,203,559 B1 | 3/2001 | Davis et al. |
| 6,206,823 B1 | 3/2001 | Kolata |
| 6,206,899 B1 | 3/2001 | Ginn |
| 6,228,025 B1 | 5/2001 | Hipps et al. |
| 6,241,740 B1 | 6/2001 | Davis et al. |
| 6,264,670 B1 | 7/2001 | Chin |
| 6,277,137 B1 | 8/2001 | Chin |
| 6,319,265 B1 | 11/2001 | Ginn |
| 6,322,499 B1 | 11/2001 | Evans et al. |
| 6,348,037 B1 | 2/2002 | Chin et al. |
| 6,350,236 B1 | 2/2002 | Hipps et al. |
| 6,406,425 B1 | 6/2002 | Chin et al. |
| 6,428,468 B1 | 8/2002 | Knighton et al. |
| 6,432,044 B1 | 8/2002 | Lunsford et al. |
| 6,436,116 B1 | 8/2002 | Spitz et al. |
| 6,436,118 B1 | 8/2002 | Kayan |
| 6,447,529 B2 | 9/2002 | Fogarty et al. |
| 6,451,035 B1 | 9/2002 | Fogarty et al. |
| 6,453,906 B1 | 9/2002 | Taylor et al. |
| 6,464,701 B1 | 10/2002 | Hooven et al. |
| 6,468,206 B1 | 10/2002 | Hipps et al. |
| 6,478,734 B1 | 11/2002 | Taylor et al. |
| 6,482,153 B1 | 11/2002 | Hipps et al. |
| 6,506,200 B1 | 1/2003 | Chin |
| 6,511,494 B1 | 1/2003 | Knighton et al. |
| 6,551,314 B1 | 4/2003 | Hill et al. |
| 6,558,313 B1 | 5/2003 | Knighton et al. |
| 6,660,016 B2 | 12/2003 | Lindsay |
| 6,709,413 B1 * | 3/2004 | Chance et al. ........... 604/6.04 |
| 6,752,756 B2 | 6/2004 | Lunsford et al. |
| 6,830,546 B1 | 12/2004 | Chin et al. |
| 6,887,251 B1 | 5/2005 | Suval |
| 6,976,957 B1 | 12/2005 | Chin et al. |
| 6,989,018 B2 * | 1/2006 | Fogarty et al. ........... 606/190 |
| 7,311,708 B2 * | 12/2007 | McClurken ............. 606/50 |
| 2003/0009132 A1* | 1/2003 | Schwartz et al. ......... 604/152 |
| 2003/0014069 A1* | 1/2003 | Fogarty et al. ........... 606/190 |
| 2003/0100920 A1* | 5/2003 | Akin et al. ............. 606/213 |
| 2003/0139758 A1 | 7/2003 | Hopper et al. |
| 2003/0225364 A1* | 12/2003 | Kraft et al. ............. 604/35 |
| 2004/0010282 A1* | 1/2004 | Kusleika ............... 606/200 |

| | | | |
|---|---|---|---|
| 2004/0092990 | A1 | 5/2004 | Opie et al. |
| 2004/0122458 | A1 | 6/2004 | Opie et al. |
| 2004/0236214 | A1 | 11/2004 | Opie et al. |
| 2004/0267163 | A1 | 12/2004 | Opie et al. |
| 2005/0004536 | A1 | 1/2005 | Opie et al. |
| 2005/0004586 | A1 | 1/2005 | Suval |
| 2005/0020940 | A1 | 1/2005 | Opie et al. |
| 2005/0021068 | A1 | 1/2005 | Opie et al. |
| 2005/0040061 | A1 | 2/2005 | Opie et al. |
| 2005/0273125 | A1 | 12/2005 | Opie |
| 2006/0235431 | A1* | 10/2006 | Goode et al. .................. 606/108 |
| 2006/0258996 | A1 | 11/2006 | Opie et al. |
| 2007/0123826 | A1 | 5/2007 | Opie |
| 2007/0129694 | A1 | 6/2007 | Opie |
| 2008/0161843 | A1 | 7/2008 | Clague et al. |
| 2008/0167669 | A1 | 7/2008 | Clague et al. |

FOREIGN PATENT DOCUMENTS

| | | |
|---|---|---|
| GB | 2 195 540 | 4/1988 |
| SU | 510235 | 4/1976 |
| SU | 1371689 | 2/1988 |
| WO | 2004/006777 | 1/2004 |
| WO | 2004/105618 | 12/2004 |
| WO | 2004/106203 | 12/2004 |
| WO | 2004/108200 | 12/2004 |
| WO | 2004/110283 | 12/2004 |
| WO | 2004/112881 | 12/2004 |
| WO | 2005/002659 | 1/2005 |
| WO | 2005/004754 | 1/2005 |

OTHER PUBLICATIONS

Dregelid, et al., "Endothelial cell injury in human saphenous veins after manipulation and tweezer grasping," J. Cardiovasc. Surg., (1988) 29(4):464-9.

DeLaria, et al., "Leg Wound Complications Associated with Coronary Revascularization," J. Thorac. Cardiovasc. Surg. (1981) 81:403-407.

Dmitri, et al., "A quick and atraumatic method of autologous vein harvesting using the subcutaneous extraluminal dissector," J. Cardiovasc. Surg. (1987) 28:103-111.

Hauer, et al., "Endoscopic subfacial discussion of perforating veins," Surgical Endosc. (1988) 2:5-12.

Meldrum-Hanna, et al., "Long Saphaneous Vein Harvesting," J. Surg. (1986) 56:923-24.

Moazami, et al., "Minimally Invasive Greater Saphenous Vein Harvesting for Coronary Artery Bypass Surgery," Surgical Rounds (1997) pg. 94-98.

Rashid, et al., "Subcutaneous Technique for Saphenous Vein Harvest," Ann. Thorac. Surg. (1984) 37(2):169-170.

"Incision Decision," Atrium Medical Corporation advertisement, appearing in J. Thorac. Cardiovasc. Surg. (1982) 83(4).

Beckering, et al, "A Method for the Autopsy Study of the Femoral-Popliteal Vessels," Am. J. Clinical Path., 47(5), 1967, 652-653.

* cited by examiner

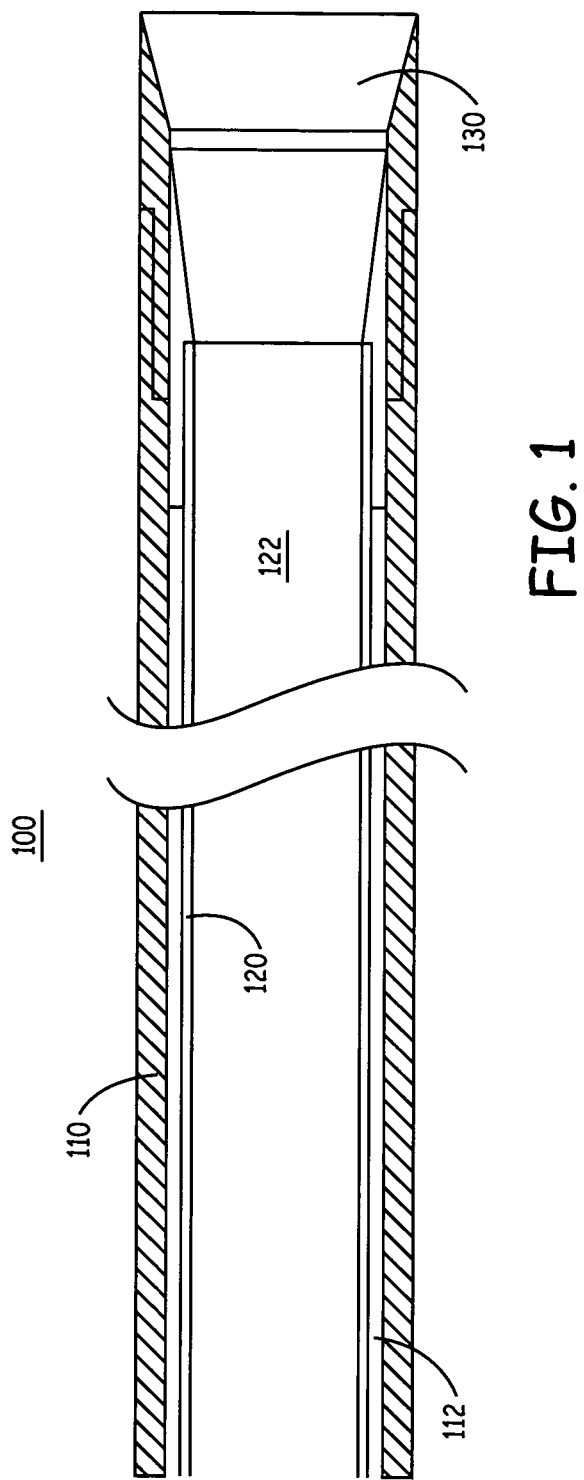

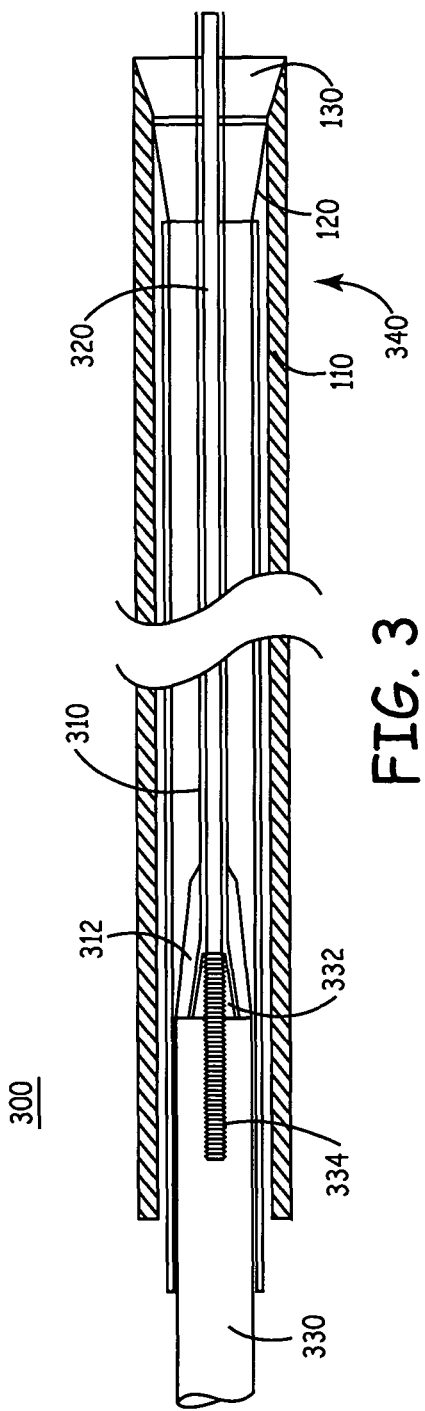

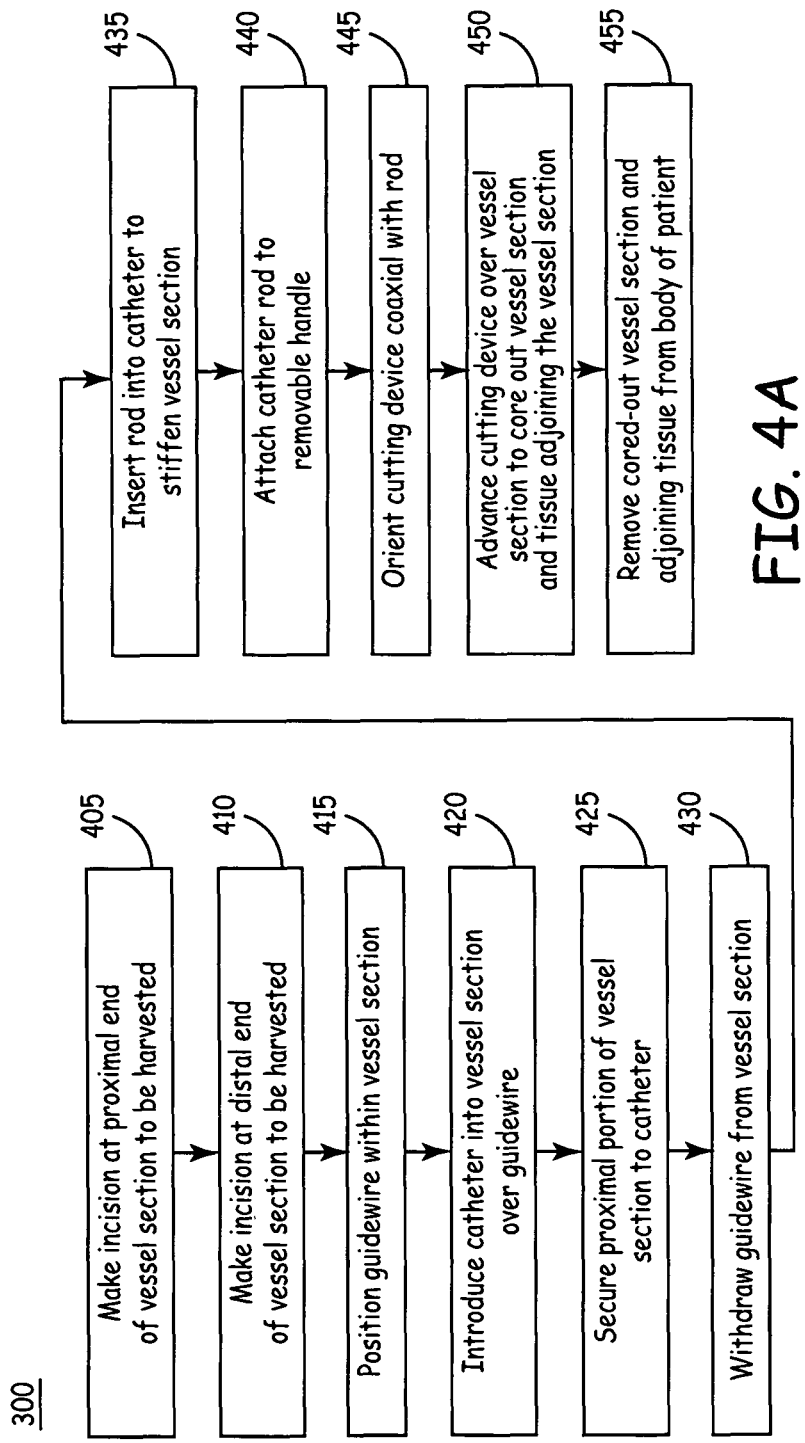

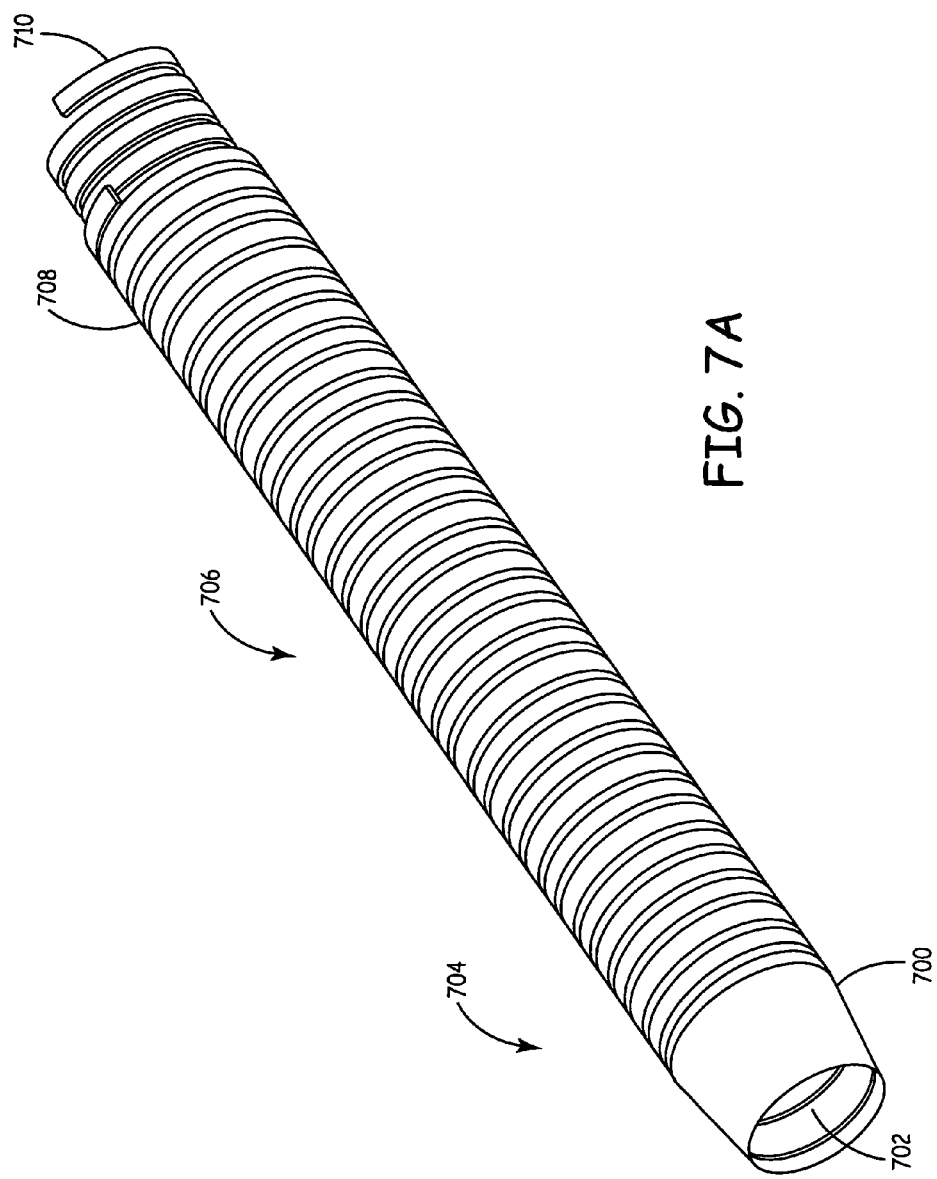

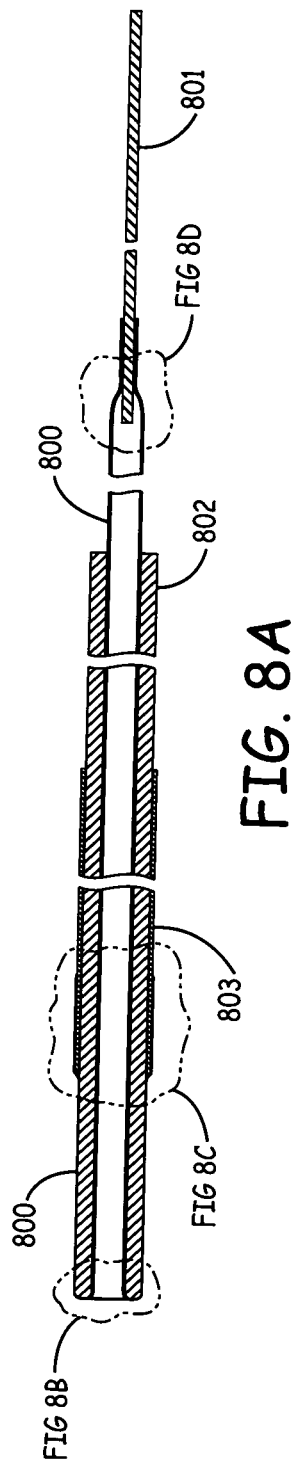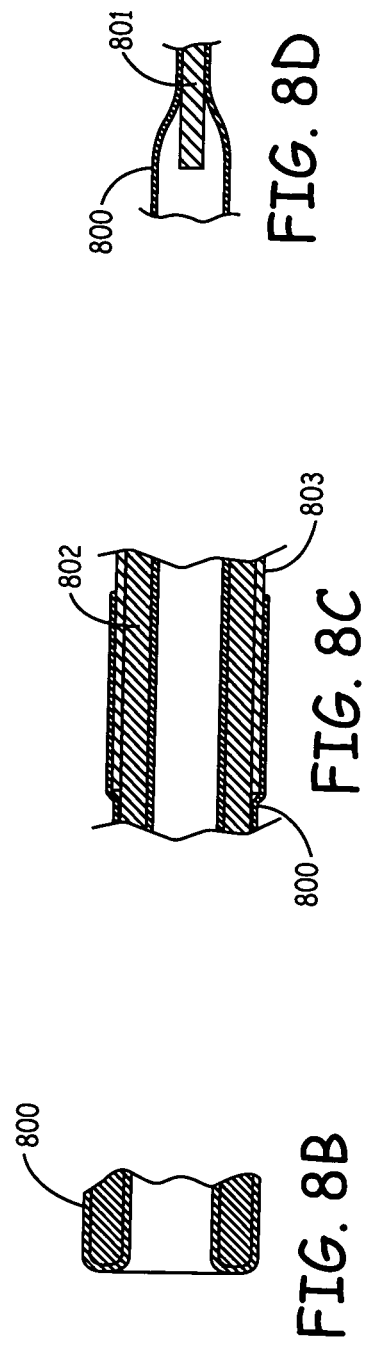

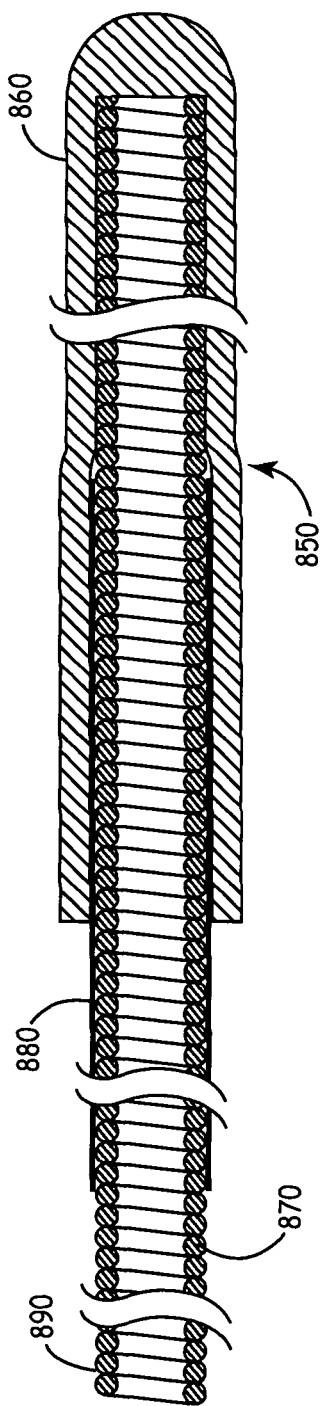

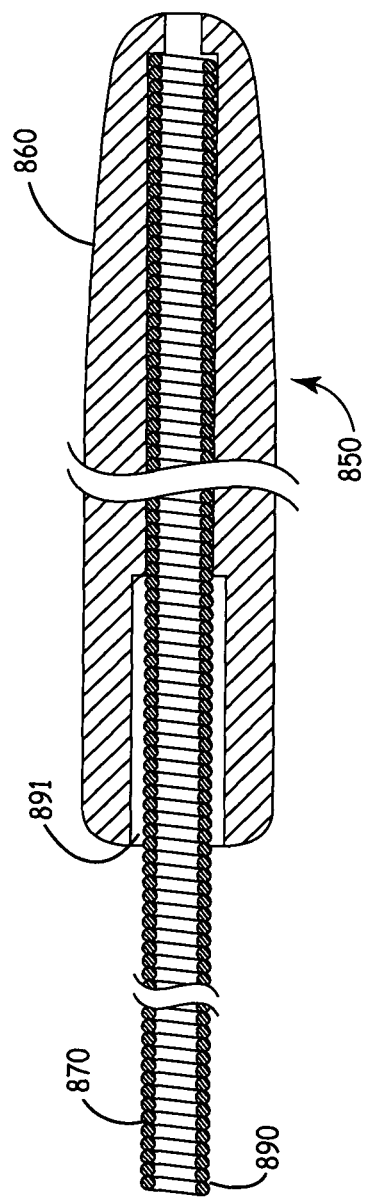

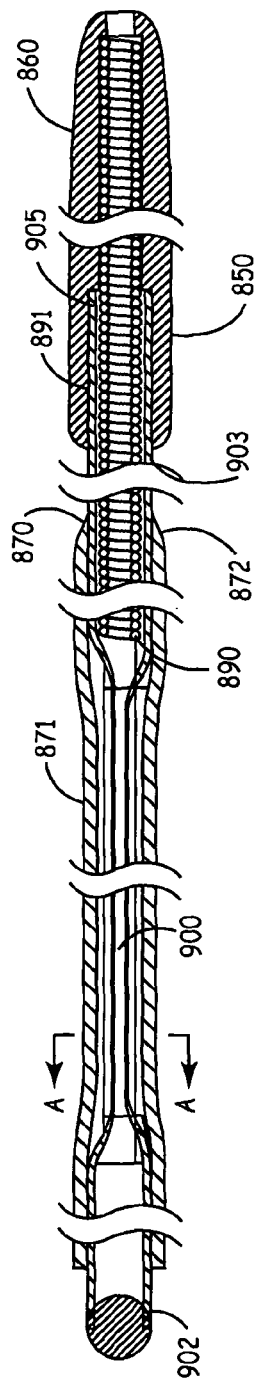
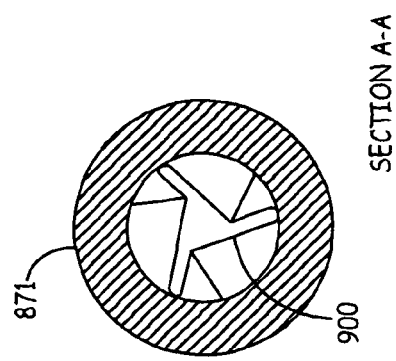
FIG. 9D
FIG. 9E
SECTION A-A

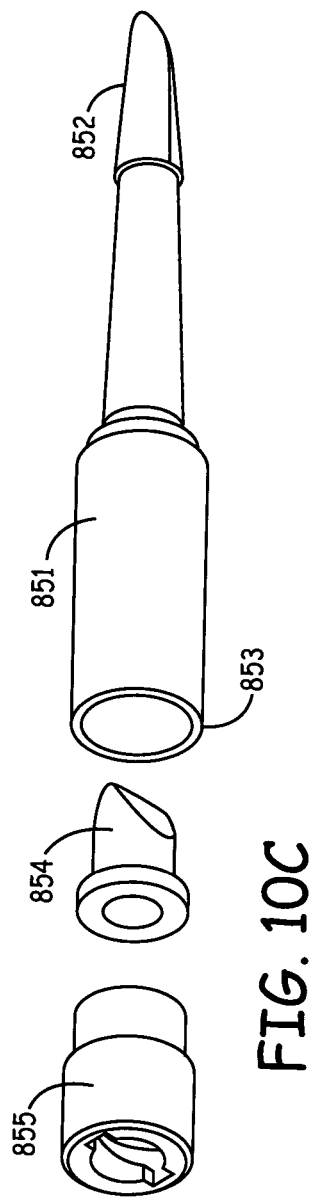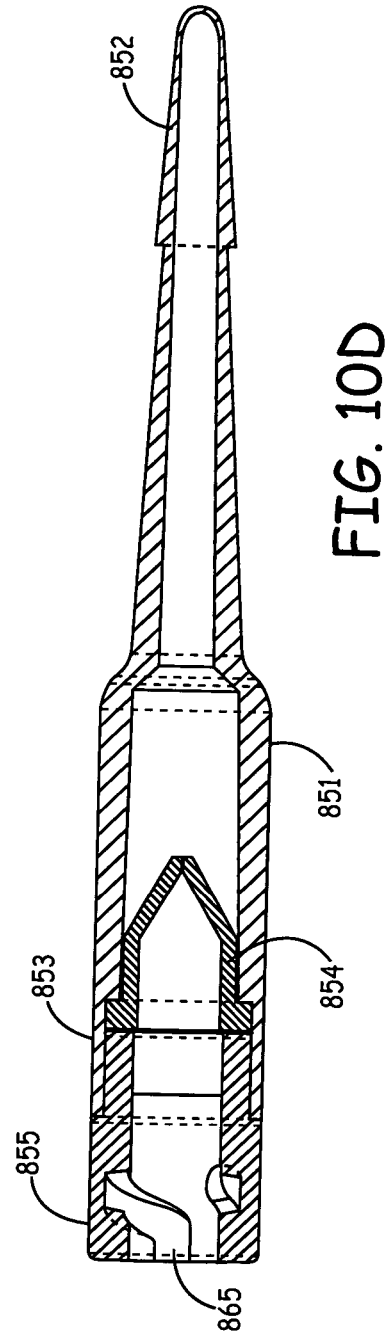

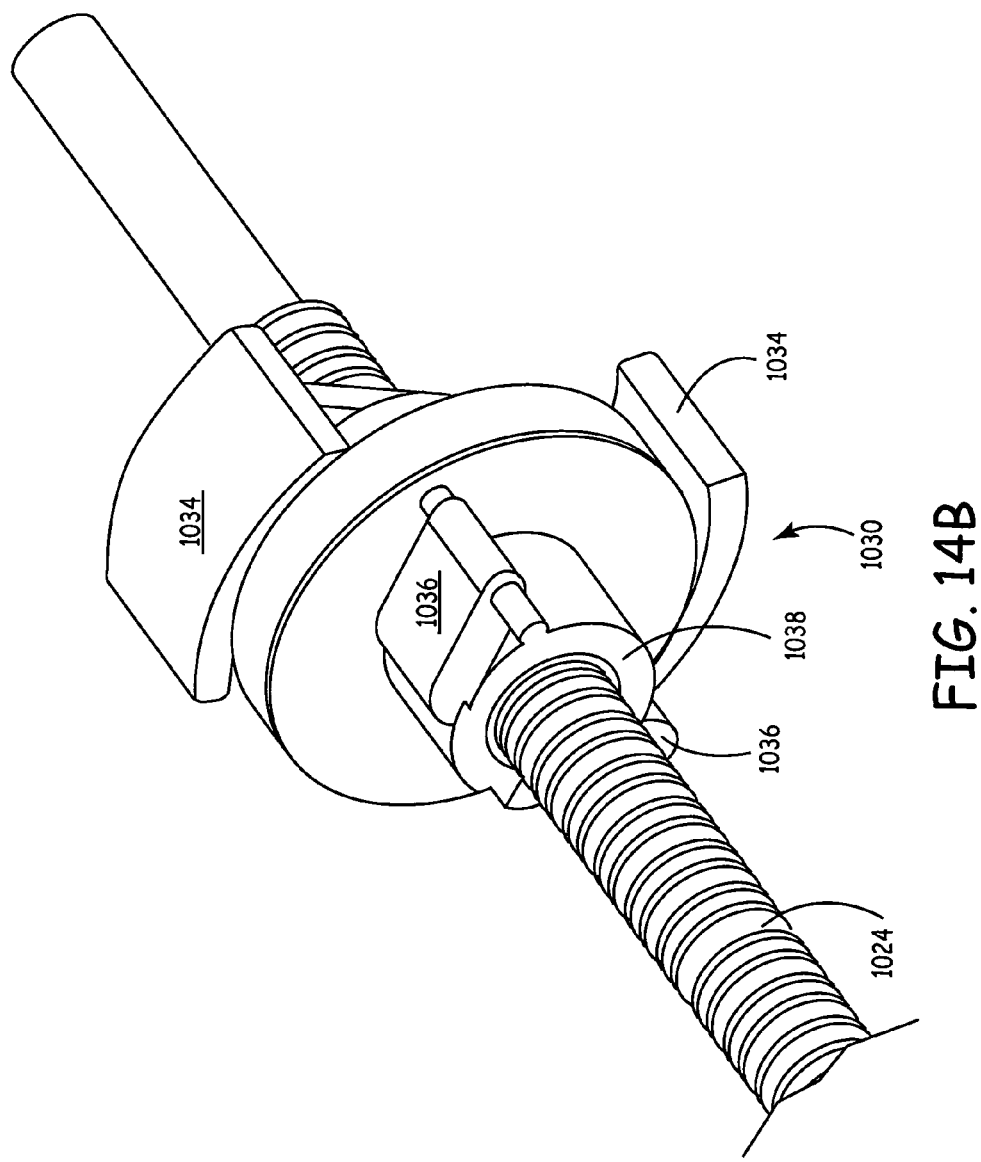

MINIMALLY INVASIVE CORING VEIN HARVESTER

CROSS-REFERENCE TO RELATED APPLICATIONS

This application claims priority to provisional U.S. Application Ser. No. 60/580,237, filed Jun. 16, 2004 titled Minimally Invasive Coring Vein Harvester, the disclosure of which is incorporated herein by reference in its entirety.

FIELD OF THE INVENTION

This invention relates generally to biomedical systems and methods. More specifically, the invention relates to systems and methods for harvesting a vessel section.

BACKGROUND OF THE INVENTION

Heart disease, specifically coronary artery disease, is a major cause of death, disability, and healthcare expense in the United States and other industrialized countries. A common form of heart disease is atherosclerosis, in which the vessels leading to the heart are damaged or obstructed by plaques containing cholesterol, lipoid material, lipophages, and other materials. When severely damaged or obstructed, one or more of the vessels can be bypassed during a coronary artery bypass graft (CABG) procedure. CABG surgery is performed about 350,000 times annually in the United States, making it one of the most commonly performed major operations.

To prevent rejection, the graft material is preferably a blood vessel harvested from elsewhere within a patient's body. The most frequently used bypass vessel is the saphenous vein from the leg. Because the venous system of the leg is redundant, other veins that remain within the patient's leg are able to provide return blood flow following removal of the saphenous vein.

Various methods have been used to harvest the saphenous vein. Until recently, the typical procedure involved making a single long incision that overlies the entire length of the vein, extending from a patient's groin to at least the knee and often to the ankle. This method results in substantial postoperative pain, with patients frequently complaining more of discomfort at the site of the leg vein harvesting than of pain from their CABG surgery wound. In addition, such an extensive incision site is subject to infection and delayed healing, especially in patients with poor circulation, which not infrequently accompanies coronary artery disease. The disfiguring scar from such a large incision is also of concern to some patients.

Less invasive procedures are preferred, and surgical devices and techniques now exist that allow the saphenous vein to be harvested through one or more small, transverse incisions along the length of the vein, generally using an endoscope. Endoscopic procedures yield reduced wound complications and superior cosmetic results compared with traditional methods of vein harvesting. However, this procedure requires considerable manipulation of the vein, has a high conversion rate when visualization is obscured by bleeding or the procedure is taking too long and often requires stitches to repair the vein following harvest. Further, it is generally tedious, time consuming, and relatively complex, requiring extensive accessory equipment and a substantial learning curve for the surgeon.

Therefore, it would be desirable to have a system and a method for harvesting a vessel section that overcome the aforementioned and other disadvantages.

SUMMARY OF THE INVENTION

One aspect of the present invention is a cutting device for harvesting a vessel section. The device comprises a tubular member having at least one cutting element positioned adjacent to its distal end. The tubular member is advanced over a vessel section to core out the vessel section and tissue adjoining the vessel section.

Another cutting device for harvesting a vessel section comprises an outer tubular member and an inner tubular member. The outer tubular member has at least one cutting element positioned adjacent to its distal end. The inner tubular member is slidably received within a lumen of the outer tubular member. The outer and inner tubular members are advanced over a vessel section to core out the vessel section and tissue adjoining the vessel section.

Another cutting device for harvesting a vessel section comprises a tubular member having at least one cutting element positioned adjacent to its distal end. The cutting element has an inner routing ridge, which acts to center the vessel section within the cutting element as the cutting element passes over the vessel section. The tubular member has a flexible distal end, which allows the distal end to bend and easily navigate along the vessel section. The tubular member is advanced over a vessel section to core out the vessel section and tissue adjoining the vessel section.

Another cutting device for harvesting a vessel section comprises a tubular member having at least one cutting element positioned adjacent to its distal end and a tensioning element. The tensioning element has a cable, which is operably coupled to the vessel section to be harvested to provide tension on the vessel section during harvesting. The tubular member is advanced over a vessel section to core out the vessel section and tissue adjoining the vessel section.

Another cutting device for harvesting a vessel section comprises a tubular member having at least one cutting element positioned adjacent to its distal end and gear systems. A planetary gear arrangement increases the users rotational input. Ratcheting gears allow for the tubular member to advance during a clockwise rotation and provide a secondary cutting stroke on a counterclockwise rotation. The tubular member is advanced over a vessel section to core out the vessel section and tissue adjoining the vessel section.

Another aspect of the present invention is a system for harvesting a vessel section. One system comprises a catheter, a rod slidably receivable within the catheter, and a tubular cutting device oriented coaxial with the rod. The catheter is positioned within a vessel section, and the rod is positioned within the catheter. The cutting device is advanced over the vessel section to core out the vessel section and tissue adjoining the vessel section.

Another system for harvesting a vessel section comprises a rod, a handle attached to the rod, and a tubular cutting device slidable over the handle. The rod is positioned within a vessel, and the cutting device is advanced over at least a portion of the handle and over the vessel section to core out the vessel section and tissue adjoining the vessel section.

Another system for harvesting a vessel section comprises a vessel support member and a tubular cutting device slidable over the vessel support member. The vessel support member is positioned within a vessel, and the cutting device is advanced over the vessel section to core out the vessel section and tissue adjoining the vessel section. The vessel support member can be any of an inflatable balloon, a dilator within a flexible sheath, a wire braid which increases in diameter, a tapered dilator, a dilator having a flexible tip, a dilator with irrigation through holes, or a dilator having a lubricious coating.

Another system for harvesting a vessel section comprises an inflatable vessel support member and a tubular cutting device slidable over the inflatable vessel support member. A neck of the inflatable vessel support member is traversed through a vessel and then used to place the vessel support member into position. Once in position, the inflatable vessel support member is inflated. The cutting device is advanced over vessel support member and over the vessel section to core out the vessel section and tissue adjoining the vessel section.

Another system for harvesting a vessel section comprises an inflatable vessel support member, a flexible sheath, and a tubular cutting device slidable over the inflatable vessel support member. A neck of the inflatable vessel support member is traversed through a vessel and then used to place the vessel support member into position. Once in position the inflatable vessel support member is inflated the sheath expanding with the support member. The cutting device is advanced over vessel support member and over the vessel section to core out the vessel section and tissue adjoining the vessel section. The vessel support member can then be deflated, wherein the flexible sheath contracts returning the vessel support member back to its original profile.

Another system for harvesting a vessel section comprises a vessel support member, a tether, a parachute, and a tubular cutting device slidable over the vessel support member. The tether is connected to the parachute at one end and the vessel support member at another. The parachute is inserted into a vessel section to be harvested. Once inserted, a fluid is injected into the vessel section to carry the parachute to the distal end of the vessel section. Once received, the tether is used to pull the vessel support member into position. Once the vessel support member is in position, the cutting device is advanced over vessel support member and over the vessel section to core out the vessel section and tissue adjoining the vessel section.

Another system for harvesting a vessel section comprises a vessel support member, a rollable sheath, a tube, and a tubular cutting device slidable over the vessel support member. The rollable sheath is advanced forward into the vessel section with the tube thus rolling out as it travels along the vessel section. The vessel support member can then be advanced into rollable sheath, which protects the endothelial layer of the vessel. The cutting device can then be advanced over vessel support member and over the vessel section to core out the vessel section and tissue adjoining the vessel section.

Another aspect of the present invention is a method for harvesting a vessel section. A first incision is made at a point corresponding to a proximal end of the vessel section to be harvested, and a second incision is made at a point corresponding to a distal end of the vessel section. A catheter is introduced into the vessel section, and a proximal portion of the vessel section is attached to the catheter. The proximal end of the vessel section is severed. A rod is inserted into the catheter to stiffen the vessel section. A cutting device is oriented coaxial with the rod and advanced over the vessel section to core out the vessel section and tissue adjoining the vessel section. The distal end of the vessel section is severed. The cored-out vessel section and adjoining tissue are removed.

In another method for harvesting a vessel section, a first incision is made at a point corresponding to a proximal end of the vessel section to be harvested, and a second incision is made at a point corresponding to a distal end of the vessel section. A catheter is introduced into the vessel section, and a proximal portion of the vessel section is attached to the catheter. A rod is inserted into the catheter to stiffen the vessel section. A proximal portion of the rod is attached to a handle. The handle carries a tubular cutting device slidably disposed on the handle. The proximal end of the vessel section is severed. The cutting device is advanced over at least a portion of the handle while maintaining a coaxial orientation between the cutting device and the rod. The cutting device is also advanced over the vessel section, coring out the vessel section and tissue adjoining the vessel section. The distal end of the vessel section is severed. The cored-out vessel section and adjoining tissue are removed.

In another method for harvesting a vessel section, a first incision is made at a point corresponding to a proximal end of the vessel section to be harvested, and a second incision is made at a point corresponding to a distal end of the vessel section. A vessel support member is introduced into the vessel section. The proximal end of the vessel section is severed. A cutting device is advanced over the vessel section, coring out the vessel section and tissue adjoining the vessel section. The distal end of the vessel section is severed. The cored-out vessel section and adjoining tissue are removed.

The aforementioned and other features and advantages of the invention will become further apparent from the following detailed description of the presently preferred embodiments, read in conjunction with the accompanying drawings. The detailed description and drawings, which are not to scale, are merely illustrative of the invention rather than limiting the scope of the invention being defined by the appended claims and equivalents thereof.

Another aspect of the current invention allows the vein to be harvested through small incisions. In one embodiment, an intravascular guide and a cutting tube are used to harvest a vessel section without the use of an endoscopic. The use of an intravascular guide also allows the harvesting method to be performed without direct visualization.

BRIEF DESCRIPTION OF THE DRAWINGS

FIG. 1 is an illustration of one embodiment of a cutting device for harvesting a vessel section in accordance with the present invention;

FIG. 3 is an illustration of one embodiment of a system for harvesting a vessel section in accordance with the present invention;

FIGS. 4A-4B are flow diagrams of alternative embodiments of a method for harvesting a vessel section in accordance with the present invention;

FIGS. 7A-J are illustrations of distal ends of a cutting device for harvesting a vessel section in an embodiment of the present invention;

FIGS. 8A-8D are illustrations of a roll-out intravascular sheath for harvesting a vessel section in an embodiment of the present invention;

FIGS. 9A-9F are illustrations of one piece intravascular catheter balloon and stylet embodiments for harvesting a vessel section in an embodiment of the present invention;

FIGS. 10A-10E are illustrations of cannula and tensioning member embodiments for use in harvesting a vessel section in an embodiment of the present invention;

FIGS. 14A-C are illustrations of a drive system for use in harvesting vessel sections in embodiments of the present invention;

DESCRIPTION OF VARIOUS EMBODIMENTS

Figure 2A:
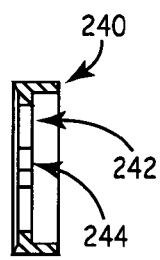
FIGS. 2A-2M illustrate various views of components for centering in accordance with the present invention.

The following discussion is presented to enable a person skilled in the art to make and use embodiments of the invention. Various modifications to the illustrated embodiments will be readily apparent to those skilled in the art, and the generic principles herein may be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention. The following introductory material is intended to familiarize the reader with the general nature and some of the features of embodiments of the invention.

One aspect of the present invention is a cutting device for harvesting a vessel section. One embodiment of the device, in accordance with the present invention, is illustrated in FIG. 1 at 100. Device 100 includes an outer tubular member 110, an inner tubular member 120, and cutting element 130.

Outer tubular member 110 is substantially rigid and is made of an appropriate biocompatible material such as a polymer or stainless steel. A distal portion of outer tubular member 110 may be flexible. For example, a section of outer tubular member 110 proximal to the cutting element(s) may include a bellows-like structure to aid in directing the cutting device over the vessel section to be harvested. (As used in this specification, "distal" and "proximal" are with reference to the operator when the device is in use.)

The length of outer tubular member 110 is based on the length of the vessel section to be harvested. For example, a length of 30 to 60 centimeters may be appropriate for harvesting a section of a typical saphenous vein. Tubular member 110 must be long enough to core out the entire vessel section desired.

The surfaces of the cutting device 100 may be coated with a material to decrease friction between the device and the tissue and between the elements of the device. The coating material could be parylene, Teflon, or other slippery, lubricious coatings.

In the present embodiment, cutting element 130 comprises an assembly having one or more blades positioned adjacent to the distal end of outer tubular member 110. The cutting element(s) may be mounted either inside or outside of outer tubular member 110. The diameter of outer tubular member 110 combined with the positioning of cutting elements 130 determines the diameter of the cored-out vessel and adjoining tissue section that is harvested. Preferably, the diameter of the core is adequate to avoid slicing the edges of the vessel being harvested as well as to transect branch vessels such that the portions of the branch vessels that remain attached to the vessel section are long enough to tie off or otherwise seal to yield a vessel section appropriate for use as a graft, for example in a CABG procedure.

Cutting element 130 is shown in FIG. 1 as having one or more straight blades. One skilled in the art will appreciate that the number and shape of cutting elements may be varied. For example, outer tubular member 110 may carry one or more of the following: a curved blade, a blade having a taper on an outside surface, a blade having a taper on an inside surface, a blade having a blunt edge on a first surface and a sharp edge on a second surface, a ring having a serrated edge, a ring having a sharpened edge, a ring having an angle, a ring having a beveled or tapered edge, a ring having a scalloped edge, two concentric rings with multiple cutting edges that pass scissor-like by each other and the like. Each cutting element would interact with the tissue surrounding the vessel in a particular way. For example, a blade having a blunt edge on the inside and a sharp edge on the outside may provide a small buffer space between the vessel and the cutting edge of the blade.

In one embodiment, inner tubular member 120 may be received within the lumen 112 of outer tubular member 110. Lumen 112 provides a close sliding fit for inner tubular member 120, allowing the inner tubular member to slide both longitudinally and rotationally within the outer tubular member. In one embodiment, inner tubular member 120 is substantially rigid and made of an appropriate biocompatible material such as a polymer or stainless steel. In one embodiment, a distal portion of the inner tubular member 120 may comprise one or more flexible materials. The flexible section of tubular member 120 may be, for example, a soft polymer, wire reinforced polymer, perforated section, bellows section or jointed section.

As seen in FIG. 1, inner tubular member 120 may be somewhat longer than outer tubular member 110 to allow the two members to be manipulated independently.

The lumen 122 of inner tubular member 120 is sized to accommodate the vessel section being harvested and may taper inwardly from the distal end, the inner diameter of a distal portion thus being larger than the inner diameter of a proximal portion. An inward taper would lightly compress the vessel section to provide better centering of inner tubular member 120 on the vessel section.

Cutting device 100 may include a component useful in positioning the device relative to the vessel to provide even better centering of the vessel within the device. FIGS. 2A-2K show examples of centering means in accordance with the present invention. The centering means may be positioned within the lumen of either the inner or the outer tubular member or within the cutting element. The centering component may also be positioned within the lumen of the cutting element 130. Positioning the centering means or component within the inner tubular member may be preferable to allow maximum freedom of movement for the inner tubular member within the outer tubular member lumen. The inner tubular member could be held still with the tissue centered while the outer tubular member is moved.

Figure 2D:
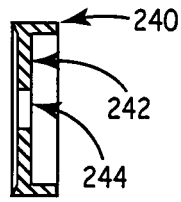
Figure 2G:
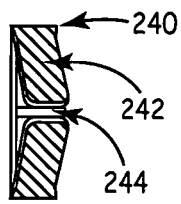
Figure 2B:
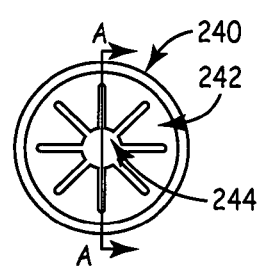
Figure 2E:
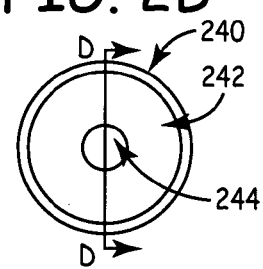
Figure 2H:
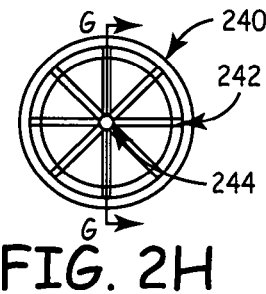
Figure 2C:
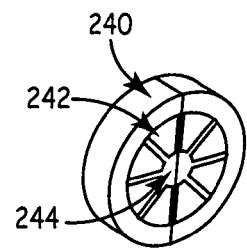

FIGS. 2A-2I show views from three angles of three different embodiments of a centering member 240 that includes centering elements 242 and apertures 244. The centering elements and apertures may assume shapes other than those shown. The centering elements 242 as shown in FIGS. 2A-2C may be flexible and thus capable of bending or being displaced as the cutting device is advanced over the vessel. If the cutting device deviates from a position centered on the vessel, one or more of the centering elements is put under greater tension than the other centering elements and, to reduce the tension, directs the cutting device back into a position centered on the vessel. Centering member 240 including centering elements 242 may comprise one or more biocompatible materials that are both flexible and resilient, for example one or more polymers or rubbers.

Figure 2F:
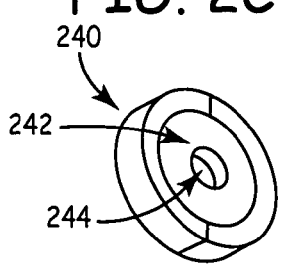
Figure 2I:
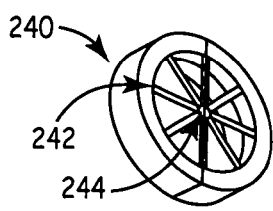

In one embodiment, centering elements 242 may comprise one or more protrusions that extend into the lumen of the inner or outer tubular member. For example, a single ring-like structure as shown in FIGS. 2D-2F may extend into the lumen near a proximal end of the tubular member. In another embodiment, as shown in FIGS. 2G-2I, multiple individual protrusions may be interspaced around the inner wall of the tubular member. Both the ring-like structure and the individual protrusions exert a force on the vessel and surrounding tissue, helping to center the vessel within the cutting device. One skilled in the art will recognize that the shape and number of protrusions may be varied to achieve maximum centering.

Figure 2J:
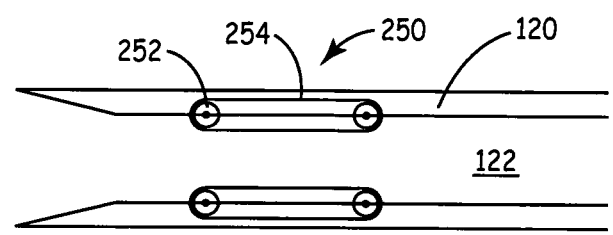
Figure 2K:
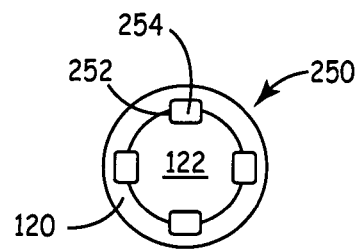

FIGS. 2J and 2K show two views of a centering member 250 that comprises bearings 252 and rollers 254. FIG. 2J is a cross-sectional side view of inner tubular member 120 showing two such mechanisms. The cross-sectional end view shown in FIG. 2K illustrates four mechanisms interspaced around inner lumen 122.

Figure 2L:
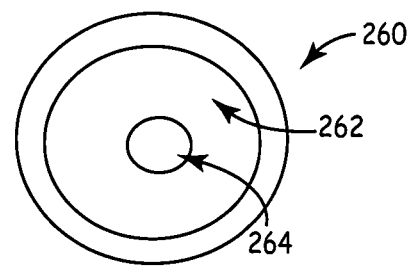
Figure 2M:
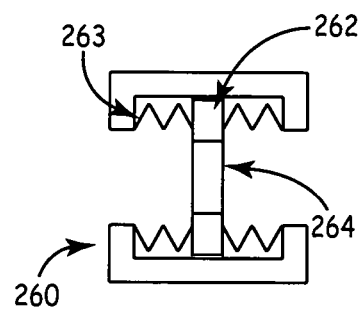

FIGS. 2L and 2M show two views of a centering member 260 that comprises centering element 262, springs 263 and an aperture 264. FIG. 2M is a cross-sectional side view of centering member 260. In one embodiment, centering element 262 may comprise a rigid plate or disk having an aperture 264. One or more pairs of springs 263 may be attached to centering element 262 and positioned around aperture 264. Springs 263 may be provided on either side of centering element 262 or on both sides of centering element 262 as shown in FIG. 2M. In one embodiment (not shown), one or more pairs of elastic members, e.g., bands, may be substituted for springs 263. Elastic members may be made of one or more rubbers or resilient-materials.

Yet another centering member (not shown) comprises a system including at least one sensor for tracking the location of the cutting device relative to a rod, a dilator, a catheter or a guidewire, for example, positioned within the vessel to be harvested. In this system, at least one Hall-effect sensor, for example, detects the presence of a metal for example, in the rod, dilator, catheter, or guidewire, placed within the vessel. Software associated with the sensor(s) displays concentric circles (or other geometrical shapes) representing the positions of the cutting device and the rod, dilator, catheter or guidewire. In one embodiment, an operator centers the device over the vessel by maintaining the circle representing the rod, dilator, catheter, or guidewire centered within the circle representing the cutting device. Alternatively, software associated with the sensor(s) may provide an audible indication of the relative locations of the cutting device and rod, dilator, catheter or guidewire. For example, the volume or pitch may change if the cutting device deviates off center with respect to the rod, dilator, catheter, or guidewire.

Yet another centering member, e.g., a balloon catheter, comprises one or more inflatable structures or elements that can be alternately inflated and deflated. The inflatable structure or structures would expand into the lumen of the inner or the outer tubular member. The expansion would force the vessel and the tissue surrounding it into the center of the member to thereby center the cutting element on the vessel. The structure or structures could be inflated to center the vessel and then the cutting element used to cut the tissue adjoining the vessel. The structure or structures may then be deflated to advance the cutting device along the vessel. After advancing the cutting device, the structure or structures may again then be inflated to center and the cutting element used to cut the tissue around the vessel. The process of incrementally inflating, cutting, deflating, and advancing may be repeated until the entire section has been excised. In one embodiment, the structure or structures may be inflated the entire time the cutting element is advanced along the vessel. Another centering embodiment comprises two magnetic or electromagnetic fields which repel each other. One intravascular field may be located within a catheter or guidewire inside the vessel and the opposing field may be located on the cutting element and/or the outer tube. The forces would repel each other keeping the cutting element and outer tube away from the inside of the vessel allowing a tissue core to be cut around the vessel without compromising the vessel.

In one embodiment, the outer 110 and inner 120 tubular members are advanced over a vessel section to core out the vessel section along with tissue adjoining the vessel section. The two tubular members can be advanced independently. For example, inner tubular member 120 may be advanced first to hold the vessel and surrounding tissue while outer tubular member 110 is advanced second to cut the tissue being held by the inner tubular member. Alternately, outer tubular member 110 may be advanced first to cut the tissue and inner tubular member 120 may be advanced second to center and hold the tissue. The process of incrementally advancing the tubular members may be repeated until the entire section of vessel has been excised. Advancing tubular member 120 ahead of outer tubular member 110 may protect the walls of the vessel from the cutting element(s) positioned on outer tubular member 110. The outer and inner tubular members may also be advanced together with the outer tubular member rotating and the inner tubular member not rotating.

Exemplary methods of advancing the tubular members include pushing and/or pulling, rotating, and twisting first in one direction and then in the other direction. In one embodiment, outer tubular member 110 and inner tubular member 120 may be twisted in opposite directions to provide a scissoring action.

Another embodiment of a cutting device in accordance with the present invention is similar to that described above and illustrated in FIG. 1, with the exception that the cutting device comprises a single tubular member that is advanced over a vessel section to core out the vessel section and tissue adjoining the vessel section. The single tubular member has one or more cutting elements positioned adjacent to its distal end. In one embodiment, a distal portion of the tubular member may extend beyond a distal end of the cutting element to protect the vessel section being harvested from being cut by the cutting elements, e.g., blade(s). The blade(s) may assume a variety of forms, including, but not limited to, a ring having a serrated edge, a ring having a sharpened edge, a straight blade, a curved blade, a blade having a taper on an outside surface, a blade having a taper on an inside surface, a blade having a blunt edge on a first surface and a sharp edge on a second surface, a ring having an angle, a ring having a scalloped edge, two concentric rings with multiple cutting edges that pass scissor-like by each other and the like. Centering members such as those described above may be positioned within the lumen of the single tubular member. A distal portion of the tubular member may be flexible to aid in directing the cutting device over the vessel section to be harvested. The flexible portion may comprise at least a portion of the cutting element.

Another aspect of the present invention is a system for harvesting a vessel section. One embodiment of the system, in accordance with the present invention, is illustrated in FIG. 3 at 300. System 300 comprises a catheter 310, a rod 320, a handle 330, and a tubular cutting device 340. The system may also include a guidewire and means for providing hemostatic control of severed branch vessels, which are not shown.

Catheter 310 and the guidewire may be made of any of a variety of biocompatible materials or combinations thereof, for example, a polymer, stainless steel, nitinol, composites, and the like. The lengths of the catheter and guidewire are roughly determined by the length of the vessel section to be harvested. The rod, catheter, and/or guidewire may be coated with a lubricious, slippery material. For example, the catheter may be coated with a slippery material to decrease friction between the catheter and the vessel to ease passage of the catheter into the vessel and decrease the possibility of damaging the vessel interior. The coating may be, for example, a hydrogel coating, polyacrylamide, polyethylene oxide, Teflon, parylene or the like. The coating may also contain one or more biological agents, such as an anticoagulant or an antithrombogenic agent to reduce clotting inside the vessel during the harvest procedure. In one embodiment, the anticoagulant may be heparin.

In one embodiment, the coating may contain one or more vasoactive agents or drugs, such as vasodilative agents or drugs and/or vasoconstrictive agents or drugs. Examples of a vasodilative drugs include, but are not limited to, a vasodilator, an organic nitrate, isosorbide mononitrate, a mononitrate, isosorbide dinitrate, a dinitrate, nitroglycerin, a trinitrate, minoxidil, sodium nitroprusside, hydralazine hydrochloride, nitric oxide, nicardipine hydrochloride, fenoldopam mesylate, diazoxide, enalaprilat, epoprostenol sodium, a prostaglandin, milrinone lactate, a bipyridine and a dopamine $D_1$-like receptor agonist, stimulant or activator. Examples of vasoconstrictive drugs include, but are not limited to, a vasoconstrictor, a sympathomimetic, methoxamine hydrochloride, epinephrine, midodrine hydrochloride, desglymidodrine, and an alpha-receptor agonist, stimulant or activator. In one embodiment, vasoactive agents or drugs may be administered via one or more bolus injections and/or infusions or combinations thereof. The injections and/or infusions may be continuous or intermittent. The injections and/or infusions may be made directly into the vessel section to be harvested.

In one embodiment, catheter 310 is strong enough to receive rod 320 within a lumen of the catheter and has an outer diameter smaller than the narrowest inner diameter of the vessel to be harvested. Catheter 310 may comprise one or more lumens. In one embodiment, catheter 310 may comprise one or more fluid openings fluidly connected to one or more lumens for delivering or introducing fluids into one or more portions of the vessel to be harvested. The one or more lumens may be fluidly coupled to one or more fluid sources. For example, one or more fluids may be introduced from one or more fluid sources into the vessel to be harvested through the one or more fluid openings prior to removing the catheter from the harvested the vessel. One or more fluids also may be introduced into the vessel through the one or more fluid openings while introducing the catheter into the vessel to be harvested. In one embodiment, suction or a negative pressure may be introduced into the vessel through the one or more fluid openings. For example, suction may be provided from a suction source coupled to the one or more lumens which, in-turn, are coupled to the one or more fluid openings to draw and hold the vessel to be harvested to the catheter while advancing the cutting device over the vessel and along the catheter. In one embodiment, catheter 310 may comprise one or more balloons, distensible members and/or inflatable members fluidly coupled to one or more lumens. Following placement of the catheter into the vessel section to be harvested, one or more inflatable members may be inflated via a gas or liquid, thereby securing the vessel to the catheter. The gas or liquid may be, for example, air, carbon dioxide, or saline. The one or more inflatable members may be inflated while advancing the cutting device over the vessel and along the catheter.

Rod 320 may be any appropriate rigid biocompatible material, for example stainless steel or a rigid polymer. In one embodiment, rod 320 is long enough to extend beyond at least the proximal end of the vessel section to be harvested and to be attached to handle 330. Handle 330 may be made of stainless steel; however, other appropriate materials such as other metals and/or suitable polymers may be used. A proximal end of catheter 310 is removably attached to handle 330. FIG. 3 shows a taper fitting 312 on the proximal end of catheter 310 that slips over a complementary taper fitting 332 on the distal end of handle 330 and secures the catheter to the handle. Other fittings, for example, a screw fitting, may also be used. In an alternative embodiment, a proximal portion of catheter 310 may instead be attached to a proximal portion of rod 320 after the rod has been inserted into the catheter. The catheter 310 may also attach to the proximal or mid-portion of the handle 330 and the vessel may attach to the distal end of the handle 330.

Handle 330 may include a cavity 334 within which a proximal portion of rod 320 is received. Cavity 334 may be contained within handle 330 as seen in FIG. 3. Alternatively, the cavity may extend through the handle, allowing the length of the portion of rod 320 that extends from the handle to be variable. A setscrew or other appropriate device may be used to secure rod 320 within cavity 334. Alternatively, a vessel cannula may be secured to the vessel. The catheter may be passed through the cannula into the vessel until a small portion remains within the cannula. The catheter may then inflated or expanded to support the vessel. The expansion in the cannula helps to hold the catheter in place. A tensioning device can then be attached to the cannula to hold the end of the vessel in place while the cutting element is advanced along the outside of the vessel.

As illustrated in FIG. 3, cutting device 340 is similar to that illustrated in FIG. 1 and described in detail above, comprising an inner tubular member 120 and an outer tubular member 110 having one or more cutting elements 130 positioned adjacent to the distal end of the outer tubular member. The two tubular members shown may be advanced independently of each other. Cutting device 340 may include means for centering the vessel within the cutting device. Exemplary centering means or devices are illustrated in FIG. 2. In an alternative embodiment, the cutting device may comprise a single tubular member having one or more cutting elements positioned adjacent to its distal end.

In the present embodiment, cutting device 340 slides over handle 330. An inner lumen of the cutting device provides a close sliding fit for the handle. As seen in FIG. 3, handle 330 extends beyond a proximal end of cutting device 340, thereby enabling an operator of the system to grasp a proximal portion of handle 330 while advancing cutting device 340 over the distal portion of the handle and over the vessel section to core out the vessel section and tissue adjoining the vessel section. Only a distal portion of handle 330 is shown in FIG. 3.

System 300 includes means (not shown) for providing hemostatic control of branch vessels severed by cutting device 340 as it is advanced over the vessel section. Various hemostatic control means are possible. For example, the hemostatic control means may comprise a biological sealant or tissue adhesive, for example a platelet gel that is prepared from the patient's blood and injected or otherwise introduced along the track of the cutting device. Alternatively, or in combination with a biological sealant, a biocompatible or biodegradable tube may be enclosed within the cutting device to be delivered as the cutting device is advanced over the vessel or after the cutting device has completed coring out the vessel and adjoining tissue. A hemostatic control tube could exert pressure on the cut branch vessels and could be either removed or, in the case of a biodegradable tube, left in place to dissolve or degrade over a period of a few days, for example. Alternatively, the exterior of the tubular cutting device may be coated with or deliver a procoagulant material such as thrombin, collagen, a thrombotic polymer, or activating agent such as kaolin or celite to promote clotting of the tissues as the device is harvesting the vessel or after harvesting the vessel. The tubular cutting device can provide a means of hemostatic control as it exerts pressure on the cut branch vessels while it remains within the patient's body. A fluid or gas, e.g. saline or carbon dioxide, may be supplied at the tip of the tool to deliver the fluid or gas into the tissue in the region where the vessel is being harvested. The supplied fluid or gas will accumulate and increase the pressure around the vessel being harvested. The increased pressure can exceed the pressure in the severed vessel branches and provide some hemostatic control by collapsing the vessels and preventing blood from exiting the severed end. A drain may be inserted at the end of the harvesting procedure to deal with any bleeding that does occur.

An alternative embodiment of a system in accordance with the present invention comprises a rod, a handle attached to the rod, and a tubular cutting device. This system is similar to system 300 described above but does not include a catheter. The rod is inserted directly into the vessel.

Yet another embodiment of the system comprises a catheter, a rod, and a tubular cutting device. Again, this system is similar to system 300, with the exception that no handle is included in this system. Instead of advancing over a handle, the cutting device is oriented coaxial with the rod. The rod, when fully inserted into the catheter within the vessel to be harvested, extends far enough outside of the vessel to allow the cutting device to be aligned over the rod. The catheter may be attached to the rod before advancing the cutting device over the rod, catheter, and vessel assembly to core out the vessel section and tissue adjoining the vessel section.

Another embodiment of the system comprises a rod or guide wire that extends beyond the distal end of the vessel and beyond the proximal end of the handle. The portion of the rod or guide wire that extends beyond the vessel to be excised and the cutting device may be used to anchor the rod or guide wire to a stable object such as a surgical table or a bedrail. An anchor device could be used to hold the rod or guide wire and a support device could be used to raise or lower the rod or guide wire to whatever height is necessary to be level with the vessel being excised. The anchor and support devices could provide a means to hold the rod or guide wire steady, straight, and level for the cutting device to follow. In one embodiment, the vessel may be attached to the catheter, rod and/or guidewire. In one embodiment, the catheter, rod and/or guidewire may be coupled to a tensioning device.

Another aspect of the present invention is a method for harvesting a vessel section. FIG. 4A shows a flow diagram of one embodiment of the method in accordance with the present invention. In this embodiment, a first incision is made at a point corresponding to a proximal end of the vessel section to be harvested (Block 405). A second incision is made at a point corresponding to a distal end of the vessel section (Block 410).

A guidewire is then positioned within the vessel section (Block 415). Alternatively, the guidewire may be inserted into the vessel before the second incision is made. Inserting the guidewire prior to making the second incision may aid in determining the optimal location for the second incision. Once the second incision has been made, the guidewire is positioned such that it extends beyond and outside of the vessel section at both the distal and proximal ends of the section.

A catheter is introduced into the vessel section over the previously placed guidewire (Block 420). A proximal portion of the vessel section is secured to the catheter (Block 425), for example by suturing the vessel onto a barb positioned adjacent to the proximal end of the catheter. Alternatively, the catheter may be introduced into the vessel without a guidewire being previously placed.

The guidewire (if present) is withdrawn (Block 430), and a rod may be inserted into the catheter to stiffen the vessel section (Block 435). Both the catheter and the rod may be attached to a removable handle (Block 440). The handle may carry a tubular cutting device, or the cutting device may be introduced over the handle after the handle has been attached to the catheter and rod. An inner lumen of the cutting device provides a close sliding fit for the handle. The tubular cutting device is thus oriented coaxial with the rod and with the vessel section to be harvested (Block 445).

The cutting device is then advanced over the vessel section to core out the vessel section and tissue adjoining the vessel section (Block 450). The cutting device may be advanced by either pushing or pulling the device over the vessel section. Where the cutting device comprises two tubular members, one positioned within the other as shown in FIG. 1, the two tubular members may be advanced separately. For example, inner tubular member 120 may be advanced first to hold the vessel and surrounding tissue, while outer tubular member 110 is advanced second to cut the tissue being held by the inner tubular member. The process of incrementally advancing the inner tubular member and then the outer tubular member is repeated until the entire section has been excised. Advancing the inner tubular member ahead of the outer tubular member may protect the walls of the vessel from the cutting element(s) positioned on the outer tubular member. Advancing and rotating the inner and outer tubular members separately may also protect the side branches of the vessel by holding them in place to achieve a clean cut at a sufficient length. The cutting device, for example, may be twisted first in one direction and then in the other direction, or it may be rotated over the vessel. The outer and inner tubular members may be twisted in opposite directions to provide a scissoring action.

The cored out vessel section and adjoining tissue are removed from the body of the patient (Block 455). Either before or after removing the vessel section and adjoining tissue, means for providing hemostatic control of branch vessels severed as a result of coring out the vessel section may be introduced through either the first or the second incision. The hemostatic control means may be, for example, a biological sealant, e.g., platelet gel that may be prepared from the patient's blood and injected or otherwise introduced along the track of the cutting device. The hemostatic control means may also be a thrombogenic substance such as fibrinogen, fibrin and/or thrombin placed in the track left by the cutting device. Alternatively, or in combination with a biological sealant, a biocompatible or biodegradable tube may be enclosed within the cutting device to be delivered as the cutting device is advanced over the vessel or after the cutting device has completed coring out the vessel and adjoining tissue. The tube exerts pressure on the cut branch vessels and may be either removed or, in the case of a biodegradable tube, left to dissolve or degrade over a period of a few days, for example. The space left after the removal of the vessel may also be filled with gauze to provide internal pressure to limit bleeding and absorb blood. The gauze may be removed periodically to check for absorbed blood. Limited blood collected on the gauze indicates the wound bleeding has diminished.

Hemostatic control means are not required for the present invention as the tubular cutting device itself can exert pressure on the cut branch vessels while it remains within the patient's body. A drain may be inserted at the end of the harvesting procedure to deal with any bleeding that does occur. The site of the vessel harvesting procedure, e.g., the leg of a patient, may also be wrapped with a compression bandage to limit bleeding.

In an alternative method in accordance with the present invention, a rod is inserted directly into the vessel. Thus, no guidewire and/or catheter is used. In one embodiment, a proximal portion of the vessel may be attached to the rod rather than to the catheter as described above. The handle is then attached to the rod.

In yet another alternative method in accordance with the present invention, the catheter is inserted directly into the vessel. Thus, no guidewire or rod is used. In one embodiment, the catheter includes one or more inflatable structures, such as balloons. In yet another alternative method in accordance with the present invention, no catheter or rod is used; only a guide wire is used.

In another embodiment of a method in accordance with the present invention, no handle is used. Instead of being carried on the handle, the cutting device is oriented coaxial with the rod. When fully inserted into the catheter within the vessel to be harvested, the rod extends far enough outside of the vessel to allow the cutting device to be aligned with the rod. The catheter may be attached to the rod before advancing the cutting device over the rod, catheter, and vessel assembly.

Figure 4B:
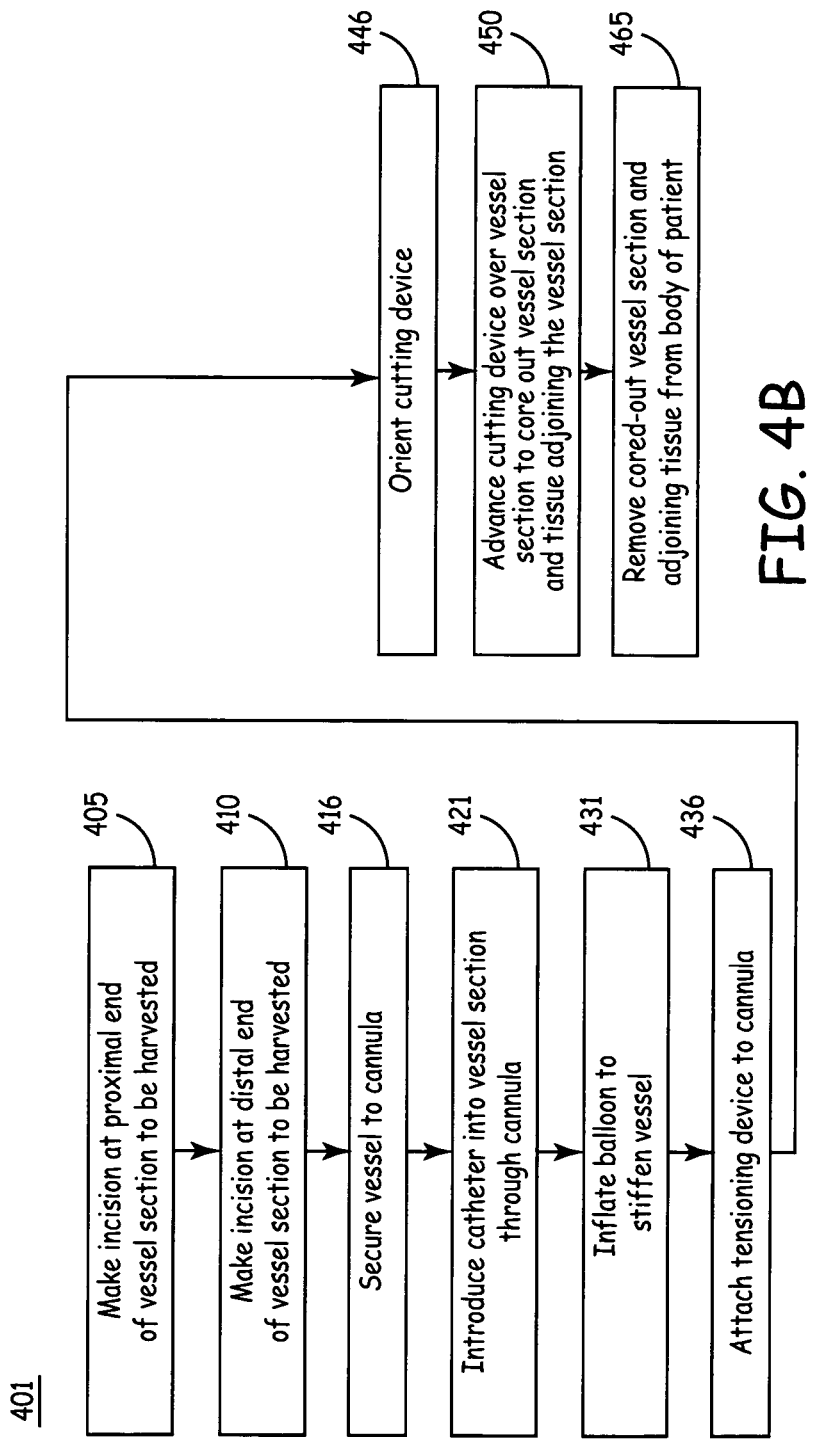

Another aspect of the present invention is an alternative method for harvesting a vessel section. FIG. 4B shows a flow diagram of one embodiment of the method in accordance with the present invention. A first incision is made at a point corresponding to a proximal end of the vessel section to be harvested (Block 405). A second incision is made at a point corresponding to a distal end of the vessel section (Block 410).

A cannula is then inserted into the proximal end of the vessel section, which is located near the knee. The proximal end of the vessel is then secured to the cannula (Block 416), for example by suturing the vessel onto a barb or raised portion positioned adjacent to the distal end of the cannula. A balloon catheter is then introduced through the cannula and positioned within the vessel section (Block 421). Once positioned, the balloon is inflated to stiffen the vessel section (Block 431). A vessel-tensioning device or system is then attached to the cannula to provide a vessel-tensioning force to the vessel section (Block 436).

A cutting device is oriented coaxially with the cannula, the balloon and the vessel section to be harvested (Block 446). The cutting device is then advanced over the vessel section to core out the vessel section and tissue adjoining the vessel section (Block 450). The cutting device, for example, may be twisted first in one direction and then in the other direction, or it may be rotated over the vessel. The cored out vessel section and adjoining tissue are removed from the body of the patient (Block 455). Either before or after removing the vessel section and adjoining tissue, means for providing hemostatic control of branch vessels severed as a result of coring out the vessel section may be introduced through either the first or the second incision. The hemostatic control means may be, for example, a biological sealant, e.g., platelet gel that may be prepared from the patient's blood and injected or otherwise introduced along the track of the cutting device. The hemostatic control means may also be a thrombogenic substance such as fibrinogen, fibrin and/or thrombin placed in the track left by the cutting device. Alternatively, or in combination with a biological sealant, a biocompatible or biodegradable tube may be enclosed within the cutting device to be delivered as the cutting device is advanced over the vessel or after the cutting device has completed coring out the vessel and adjoining tissue. The tube exerts pressure on the cut branch vessels and may be either removed or, in the case of a biodegradable tube, left to dissolve or degrade over a period of a few days, for example. The space left after the removal of the vessel may also be filled with gauze to provide internal pressure to limit bleeding and absorb blood. The gauze may be removed periodically to check for absorbed blood. Limited blood collected on the gauze indicates the wound bleeding has diminished.

Figure 5:
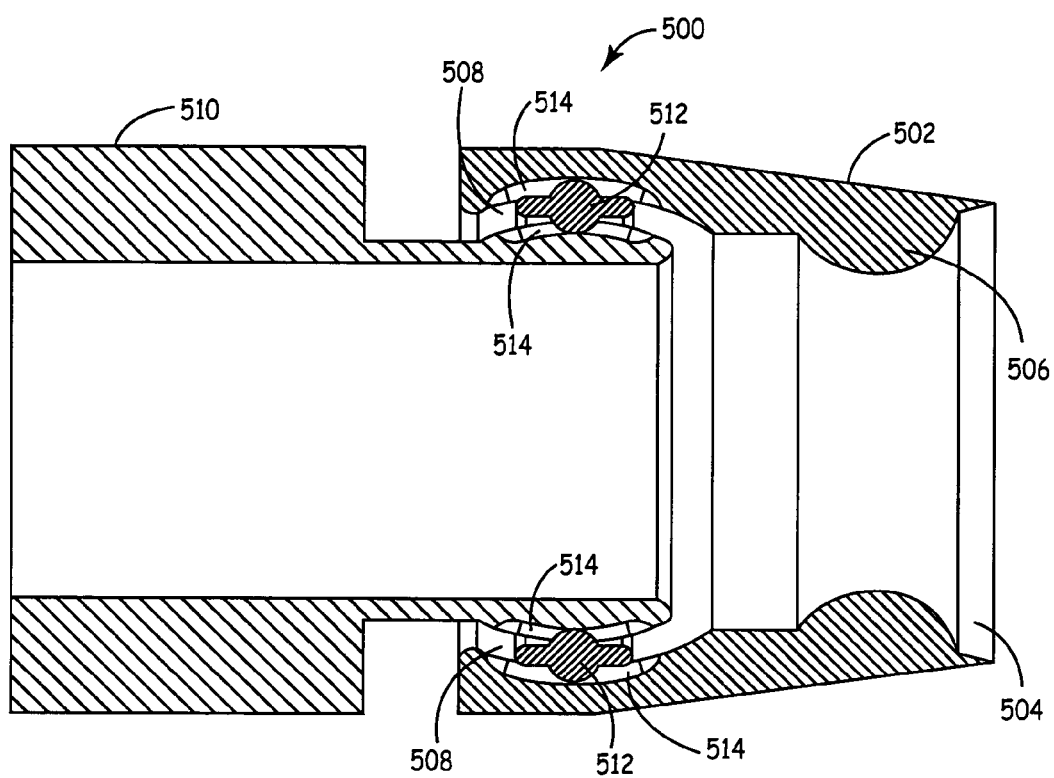
FIG. 5 is an illustration of a distal end of a cutting device for harvesting a vessel section in an embodiment of the present invention.
Figure 6:
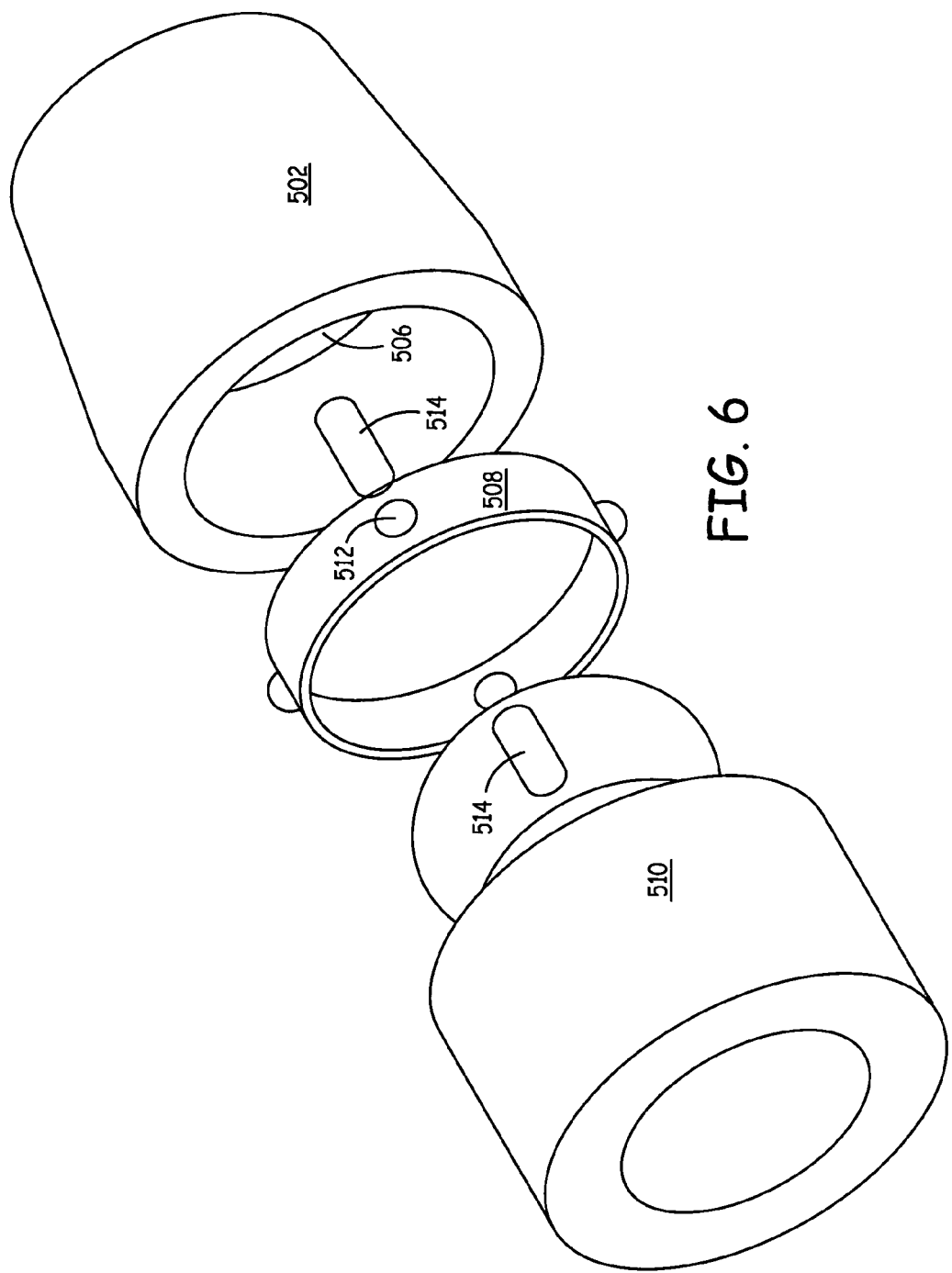
FIG. 6 is an exploded illustration of a distal end of a cutting device for harvesting a vessel section in an embodiment of the present invention.

With reference to FIG. 5, an illustration of a distal end of a cutting device for harvesting a vessel section in an embodiment of the present invention is shown. Distal end 500 of cutting device 502 is comprised of cutting element 504, routing ridge or ring-like structure 506, connector section 508, and tubular member 510. As shown, tubular member 510 is operably coupled to centering member 502 via connector section 508. Connector section 508 has rounded surface features 512, which fit within grooves 514 and hold tubular member 510 to centering member 502 (FIG. 6). The relationship of the grooves 514 and the surface features 512 allows the centering member 502 tip off axis from tubular member 510 and allows cutting device 502 to be coupled to tubular member 510 so that 502 rotates as 510 is rotated.

Regardless of what device is being used to stabilize or support the vessel, routing ridge 506 is designed to contact the tissue being cut and to meet resistance against the stabilizing or support device inside the vessel. The contact and resistance exerted against routing ridge 506 pushes on the cutter device to center centering member 502 around the vessel. Thus, as tubular member 510 is advanced over the vessel, if the vessel is curved in any way, routing ridge 506 will contact the vessel first before the cutting element 504, thereby centering cutting element 504 over the vessel prior to cutting element 504 coming into contact with the vessel and thus avoiding any damage to the vessel.

With reference to FIGS. 7A-7J, illustrations of distal ends of a cutting device for harvesting a vessel section in various embodiments of the present invention are shown. In these figures cutting element 700 and routing ridge 702 at distal end 704 are similar in structure to embodiments of FIGS. 5 and 6. However, the embodiments of FIGS. 7A-7J provide a flexible distal end 704 to assist cutting device 706 in navigating over a vessel during harvesting. Each distal end 704 has a construction, which allows for the distal end to bend or flex and thus more easily navigate around curvatures of the vessel. Distal end 704 is designed to provide increase tracking response and flexibility.

Figure 7B:
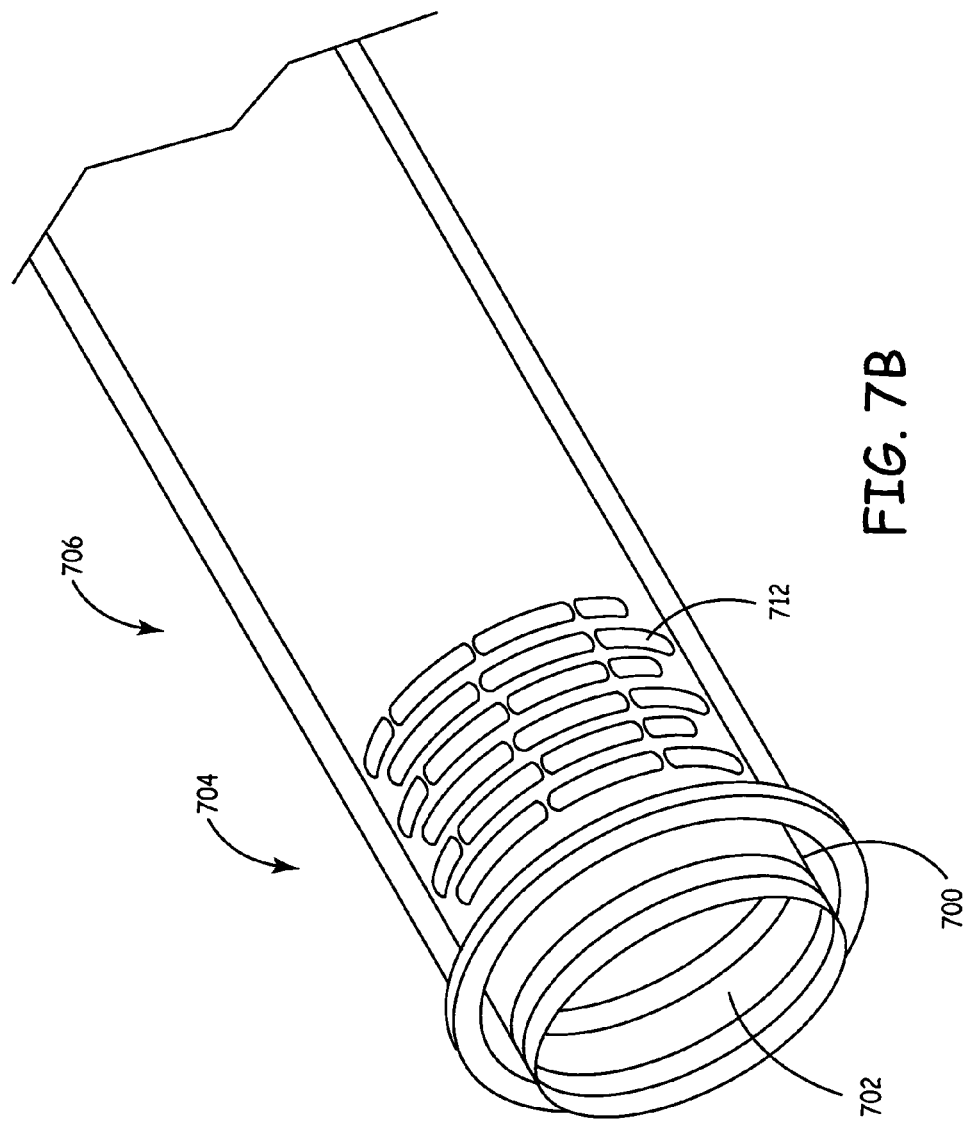
Figure 7C:
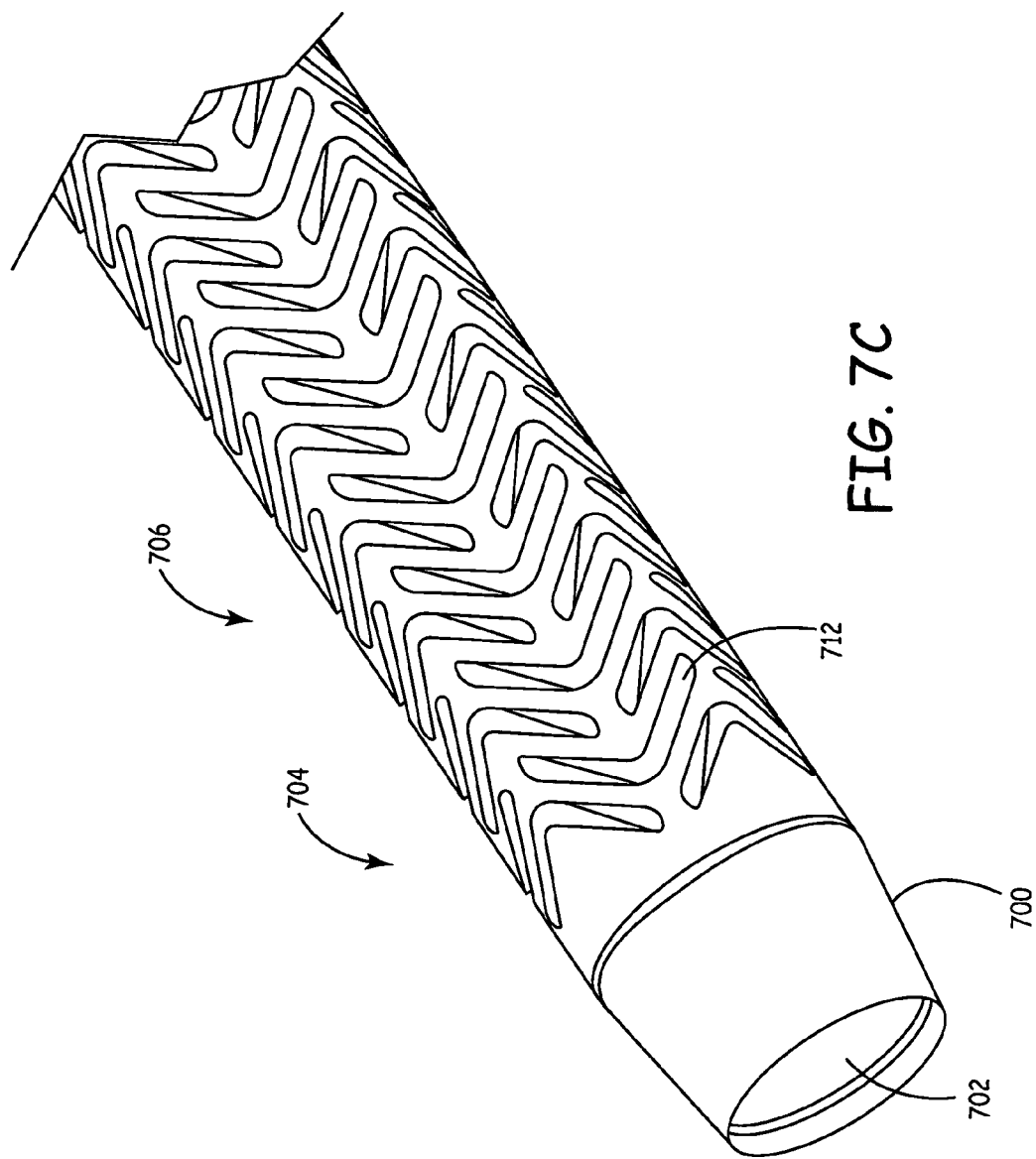
Figure 7D:
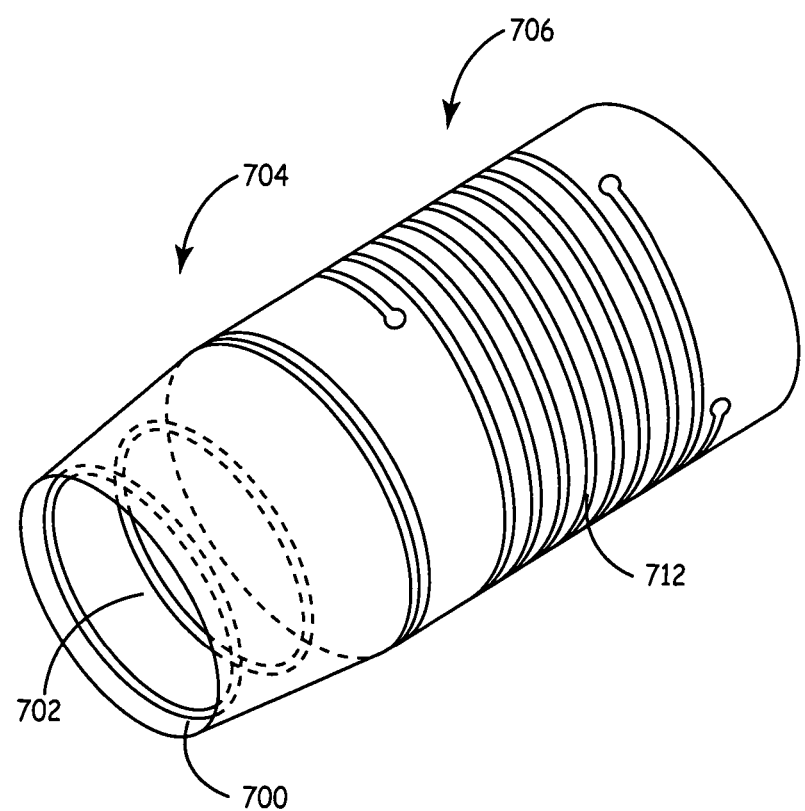
Figure 7E:
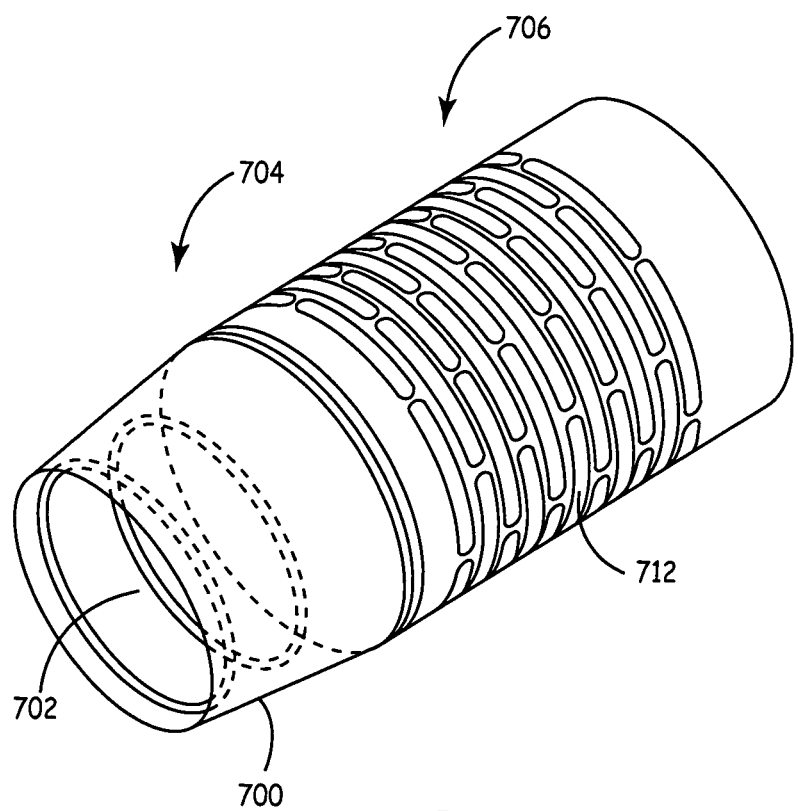
Figure 7F:
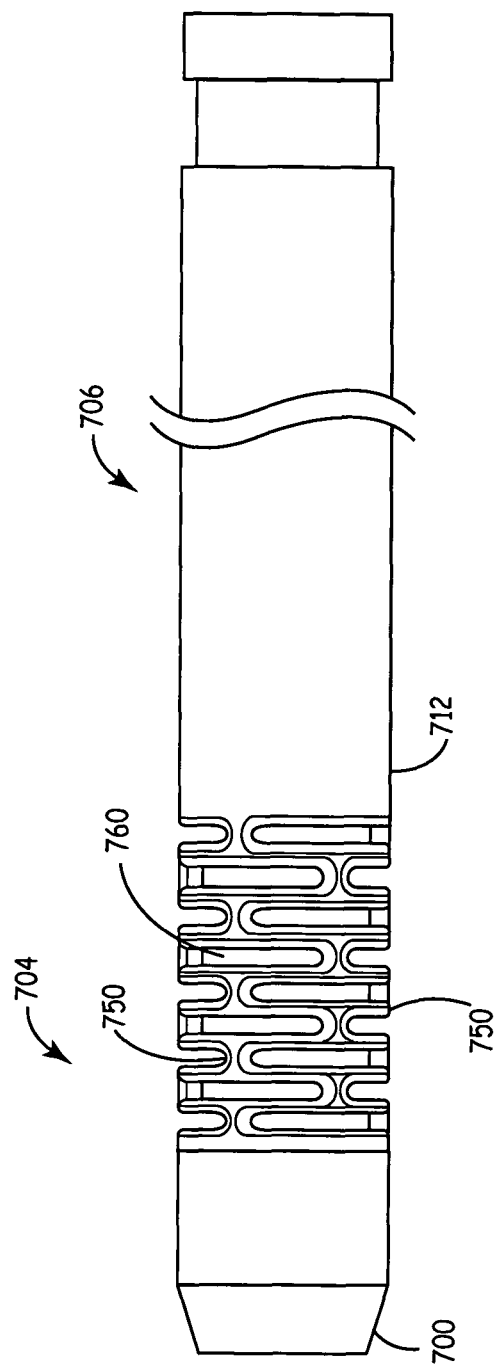
Figure 7G:
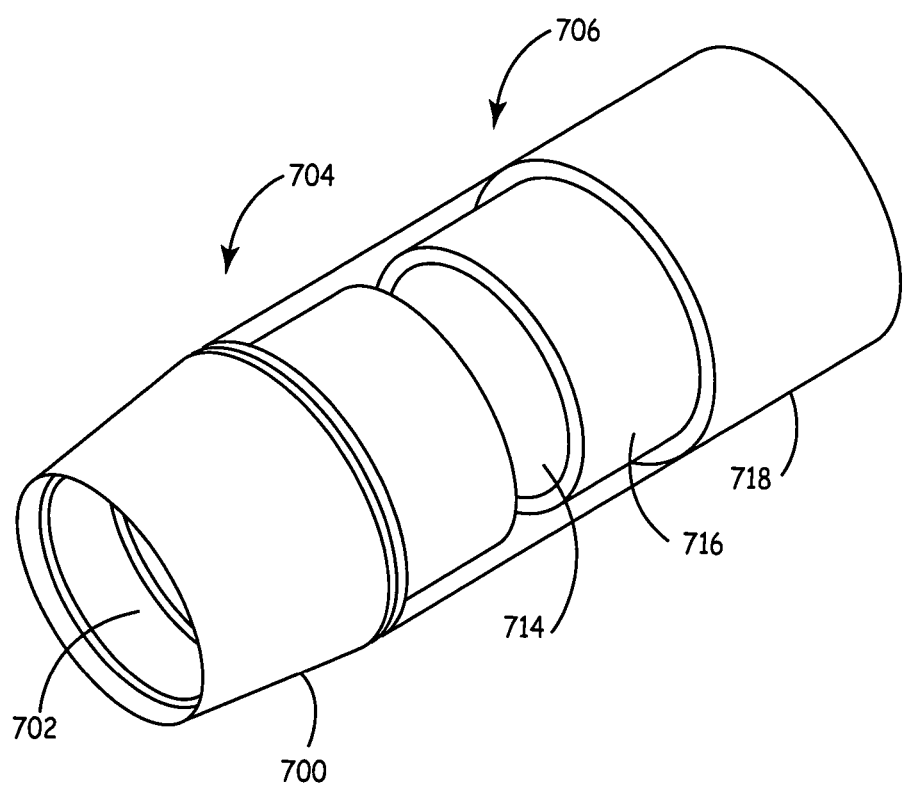
Figure 7H:
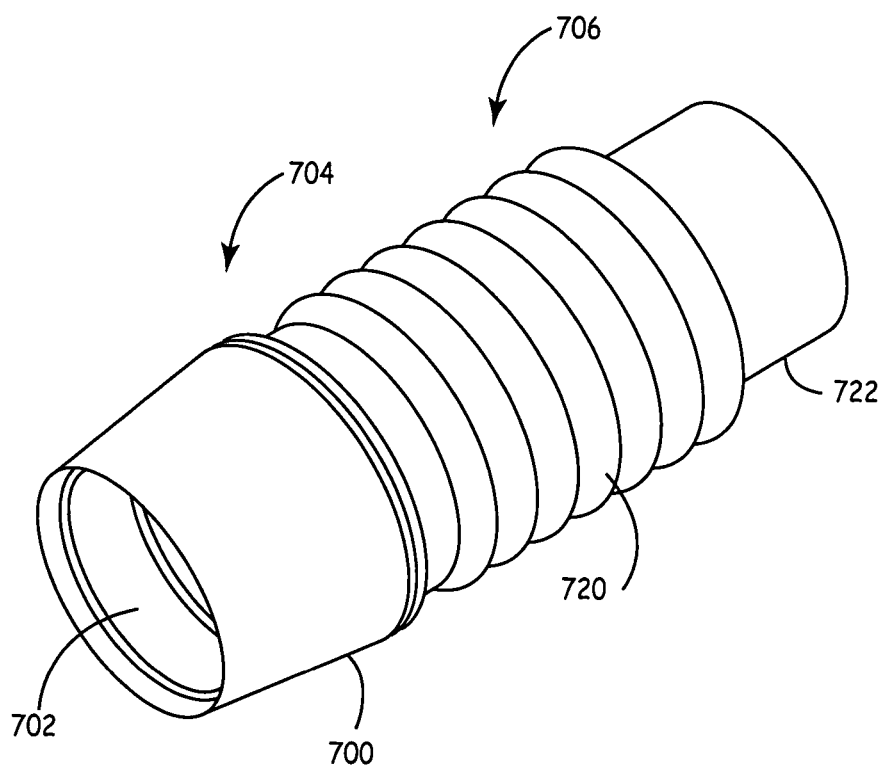
Figure 7I:
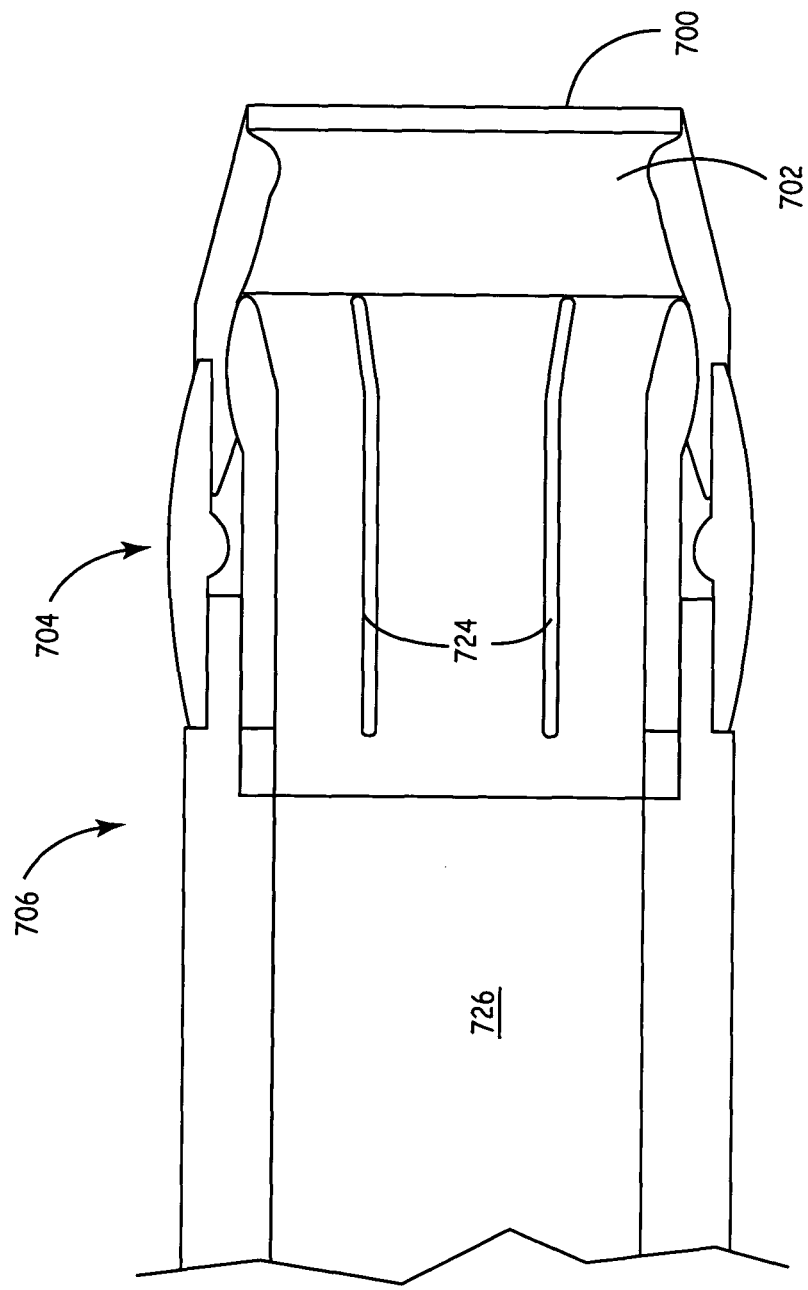
Figure 7J:
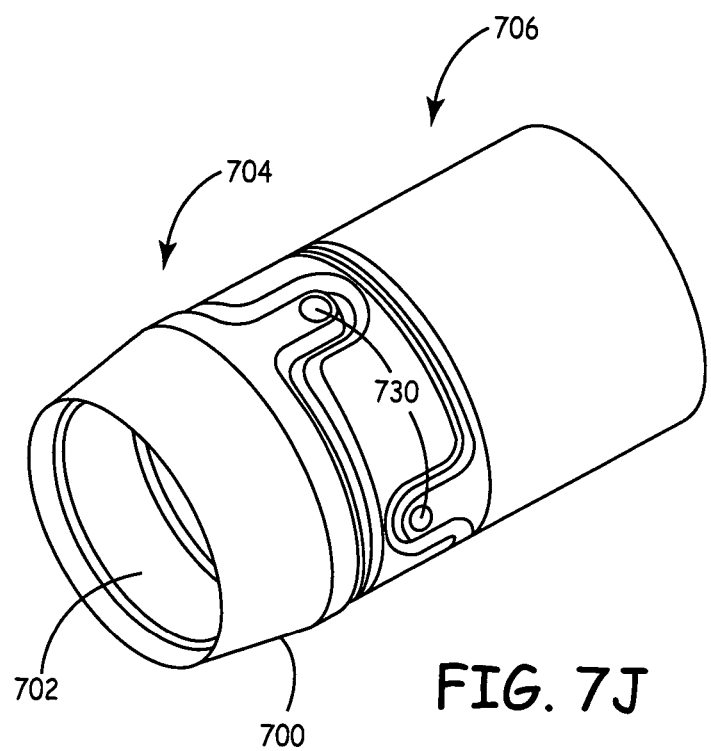

The embodiment of FIG. 7A utilizes a dual coiled structure having a counter clockwise wound outer coil 708 and a clockwise wound inner coil 710. The dual coil structure provides for a torsionally stable tube strong enough to withstand external compression, yet still remain flexible due to the coil nature. FIGS. 7B-7F show various perforated tube sections. These perforations or slots weaken the tubing wall just enough to allow the tubing to be flexible enough to route cutting device 706 around the vessel, especially curved vessels. Perforated tubing 712 can be made from a biocompatible metal, such as stainless steel, or a biocompatible plastic, such as polyurethane, acrylic, polyvinylchloride (PVC) and/or similar material. This perforated geometry proves for good flexibility and high torque. The portions in the perforated sections that run coaxially with the center of the tubular member, i.e., the posts, facilitate providing torque. In FIG. 7F, posts 750, beams 755 and perforated slots 760 increase in size from the distal portion to the proximal portion. This variation in size stimulates a tapered beam, e.g., a fishing pole, to allow for the greatest flexibility at the distal end while distributing the stress along its length. In FIG. 7G, multiple tubes 714, 716, and 718 are used to provide the flexible distal end 704. As shown, each tube 714, 716, and 718 terminate at a different proximal distance than the other. Each tube could be made of a biocompatable material, such as ePTFE (expanded polytetrafluoroethylene), silicone, polyvinylchloride and/or similar material, which is a very flexible material that keeps its shape when compressed and extended axially. Tube 714 extends to cutting element 700, tube 716 terminates a distance proximal of cutting element 700, and tube 718 terminates a further distance proximal to cutting element 700. By wrapping tubes 714, 716, and 718 around one another the amount of torque that can be applied to cutting device 706 can be increased. But as the tube diameter decreases towards distal end 704, distal end 704 becomes more flexible and thus able to navigate over vessels having small to large curvature. In FIG. 7H, a flex straw embodiment is utilized. Flex straw portion 720 may be made from the same material as tubing 722 providing that the material is biocompatible and has good flexing capabilities. Flex straw portion 720 provides a good torque quotient in that portion 720 can be compressed to solid, but yet provides for good flexibility when not compressed. FIG. 7I shows an embodiment where perforations 724 run lengthwise along tubing member 726. FIG. 7J shows cutting device 706 having multiple universal joints 730 and 732 to provide for flexible distal end 704. Universal joints 730 provide for flexibility in a vertical plane while joints 732 provide for flexibility in a horizontal plane. It is fully contemplated that distal end 704 could have other designs providing distal end flexibility without departing from the spirit of the invention. It is also further contemplated that distal end 704 could be manufactured from most any biocompatible material including metals, ceramics, and plastics without departing from the spirit of the invention.

With reference to FIGS. 8A-8D, illustrations of a rollout intravascular sheath for harvesting a vessel section in one embodiment of the present invention are shown. Rollout intravascular sheath 800 can be used to introduce a stabilizing or support device, as discussed above and in more detail below, into a vessel while protecting the endothelial layer of the vessel. Sheath 800 is designed to provide support to the vessel during a vessel harvesting procedure, e.g., a saphenous vein harvesting procedure. Rollout sheath 800 is a flexible tube, which is shown not fully extended in FIGS. 8A-8D. A rigid or semi-rigid inner tube 802 is shown advanced partially through the sliding sleeve 803. Prior to advancing tube 802 through sliding sleeve 803, sheath 800 is everted around the edges of the sliding sleeve 803 and one end is fixedly attached or bonded to the sliding sleeve 803, as shown in FIG. 8C. The other end of sheath 800 is fixedly attached or bonded to one end of a wire 801, as shown in FIG. 8D. Tube 802 is advanced over wire 801, over a portion of sheath 800 and through sliding sleeve 803. Tube 802 is advanced forward into rollout sheath 800 and into the vessel section to be harvested. Advancement of tube 802 causes flexible rollout sheath 800 to unroll as it enters the vein. Wire 801 is free to move with sheath 800 while tube 802 is advanced forward thereby allowing sheath 800 to be unrolled. In the current embodiment, there is little to no relative motion, or sliding between sheath 800 and the interior wall of the vessel. Unrolling sheath 800 within the vessel can minimize damage to the endothelial lining of the vessel as compared to sliding a member against the endothelial lining of the vessel as the member is advanced through the vessel.

Sheath 800 can be made of most any biocompatible material, such as polyurethane or ePTFE, without departing from the spirit of the invention. With the rollout embodiment, as the clinician advances tube 802 in the vessel, sheath 800 material is rolled out. While tube 802 is advanced in the vessel, the sliding sleeve 803 is held stationary, e.g., just outside the vessel at a point adjacent the site of vessel insertion. Tube 802 is advanced in the vessel to a length that corresponds to the length of vessel that is intended to be harvested. To remove the sheath 800 from the vessel, wire 801 is pulled back, thereby retracting sheath 800 and tube 802 from the vessel and, thereby creating no relative motion between sheath 800 and the vessel.

Figure 9A:
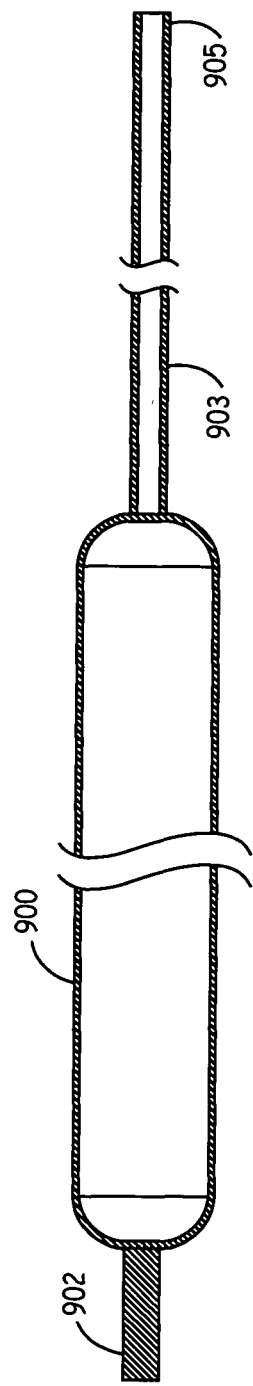

With reference to FIG. 9A, an illustration of a one-piece intravascular balloon catheter for harvesting a vessel section in one embodiment of the present invention is shown. This embodiment provides for an intravascular balloon catheter 900 that is plugged at its proximal end 902 and has an extended unexpanded balloon material. Balloon catheter 900 may be approximately 300-500 mm long with a 1.0-2.0 mm diameter when folded and 2.0-6.0 mm diameter when inflated. The balloon catheter 900 may be made of most any biocompatible material, such as nylon, urethane, polyethylene, or PET, for example, without departing from the spirit of the invention. The elongated distal end or routing end 903 of balloon catheter 900 is used to navigate balloon catheter 900 through the vessel and into place.

A stylet 850, shown in FIG. 9B, may be placed within routing neck 903 of balloon catheter 900 to prevent kinking of routing neck 903 during insertion and routing of neck 903 within the vessel. In one embodiment, stylet 850 includes a flexible tip or cap 860 at its distal end, a coiled wire 870, and a membrane 880. Flexible tip 860 helps to minimize damage to the vessel wall when navigating around curves. Flexible tip 860 may be tapered to allow easy insertion into vessels of varying size. The proximal end 890 of stylet 850 is positioned within routing neck 903 of balloon catheter 900. The distal end 905 of balloon catheter 900 is advanced over coiled wire 870 and over membrane 880, thereby creating a pressure fit between the distal end 905 of routing neck 903 and the membrane 880 of stylet 850. The pressure fit couples the stylet and the balloon catheter together. The coupled stylet and balloon catheter together may be navigated and routed through the vessel section to be harvested. In one embodiment, as shown in FIG. 9C, stylet 850 includes a flexible tip or cap 860 at its distal end and a coiled wire 870. The proximal end 890 of stylet 850 is positioned within routing neck 903 of balloon catheter 900. In this embodiment, the distal end 905 of balloon 900 is positioned within cavity 891, thus coupling or securing the distal end 905 of routing neck 903 and to the stylet 850, see FIG. 9D.

In one embodiment, a flexible sheath 871 may be placed over balloon catheter 900, as shown in FIGS. 9D-9E. The flexible sheath 871 is made of an elastic or resilient material capable of allowing the balloon to be expanded or inflated and also helping to deflate or collapse the balloon into a low profile configuration similar to the balloon's original configuration so that the balloon can be easily removed from the vessel. FIG. 9E shows a cross-sectional view of deflated balloon 900 within flexible sheath 871. In one embodiment, balloon 900 is in a folded configuration when it is in a deflated or collapsed configuration within flexible sheath 871.

Figure 10A:
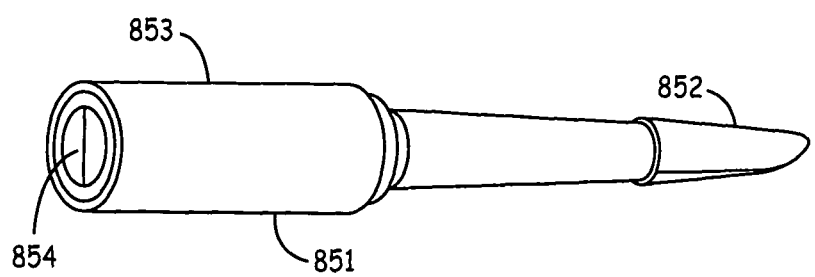
Figure 10B:
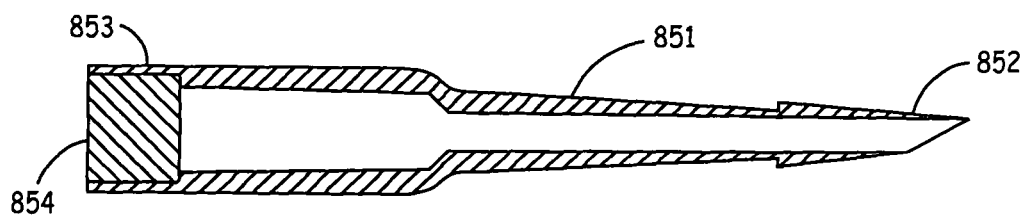
Figure 10E:
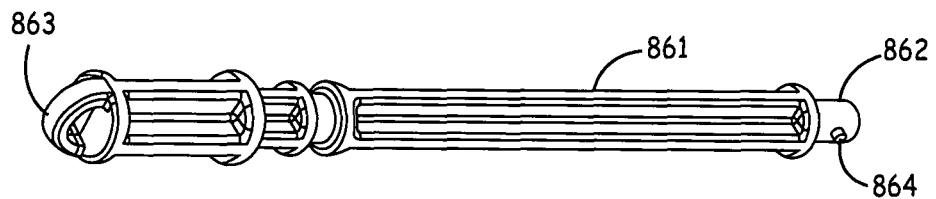

In one embodiment, the vessel section to be harvested is isolated at its proximal and distal aspects. In one embodiment, a saphenous vein section is isolated having a proximal end located approximately near the knee while the distal end is located at or near the groin region. The distal tip 852 of cannula 851, shown in FIGS. 10A-10D, is inserted into the proximal end of the isolated vessel, e.g., a section of saphenous vein. The vessel is then ligated to the cannula. The proximal end 853 of cannula 851 may include a valve 854 to prevent back flow of fluid, such as blood and/or saline, from the vessel out the cannula 851 end. In one embodiment, the valve is a bileaflet or duckbill valve, as shown in FIGS. 10A-10D. In one embodiment, the proximal end 853 of cannula 851 may include a tension-coupling member 855 for coupling a tensioning member to the cannula, shown in FIGS. 10C-10D. In one embodiment, a twist lock mechanism may be used to secure a vessel-tensioning device member 861, shown in FIG. 10E, to the cannula 851. The distal end 862 of vessel-tensioning device member 861 is inserted, twisted and locked into place within tension coupling member 855 located at the proximal end 853 of cannula 851. In one embodiment, a bayonet fastener mechanism may be used to couple member 861 to member 85. For example, raised bumps 864 sized to fit within grooves 865 may be used to couple member 861 to member 855. A vessel tensioning device or system may be coupled to vessel-tensioning device member 861 at its proximal end 863.

Once the vessel is cannulated balloon catheter 900 is routed through the vessel by routing proximal neck 903 and stylet 850 through cannula 851 and through the vessel section to be harvested. Once balloon catheter 900 is positioned in its desired location within the vessel section to be harvested, stylet 850 may or may not be removed from routing neck 903. Following placement of balloon catheter 900 within the vessel, balloon catheter 900 may be inflated through the distal end of routing neck 903, which has exited out the distal end of the vessel section. In one embodiment, balloon catheter 900 is inflated to a diameter of approximately 4 mm. Balloon catheter 900 is semi-rigid when it is inflated, which allows the vessel to still maintain most of its anatomical course. When balloon catheter 900 is inflated it is rigid enough to interface with routing ridge 506, as discussed above. Routing ridge 506, in combination with a cutting device having a flexible distal end, as discussed above, allows the cutting device to accurately and precisely navigate the vessel to ensure the harvesting of a viable vessel section, e.g., acceptable for use as a graft in a CABG procedure.

Balloon catheter 900 may or may not be made out of non-compliant or semi-compliant materials such as PET (polyethylene terepthalate), nylon, Pebax and/or polyurethane, for example. Most commonly, balloon catheter 900 is folded and wrapped in a collapsed configuration to create a low profile to assist in its insertion into the vessel. Sheath 871 may be a section of tubing made of an elastomer such as silicone and/or modified silicone, such as C-flex, which is silicone modified styrenic thermoplastic elastomer. Sheath 871 may be applied over the top of balloon catheter 900. Sheath 871 expands with balloon 900 when balloon 900 is inflated with saline solution, and returns balloon 900 back to its original low profile when balloon 900 is deflated. Thus, sheath 871 assists in an application where balloon 900 is to be inserted into a vessel with a low profile, inflated, and removed from the vessel with a low profile.

By returning the vessel to a low profile after it has been inflated inside a vessel, the amount of damage to the inner vessel walls is greatly reduced during removal of balloon catheter 900. Non-compliant and semi-compliant balloons are often folded and wrapped so that they have the lowest possible profile until they reach their destination within the vessel. Then once balloon 900 reaches its desired area it is inflated. Then in order to remove balloon 900 from the vessel, balloon 900 is deflated. However, balloon 900 may not return to its original low profile shape when deflated. This can be destructive to the inner walls of the vessel as balloon 900 can have edges created by folds when balloon 900 is deflated. Therefore, the elasticity of sheath 871 is used to bring the deflated balloon back to its original profile.

Figure 9F:
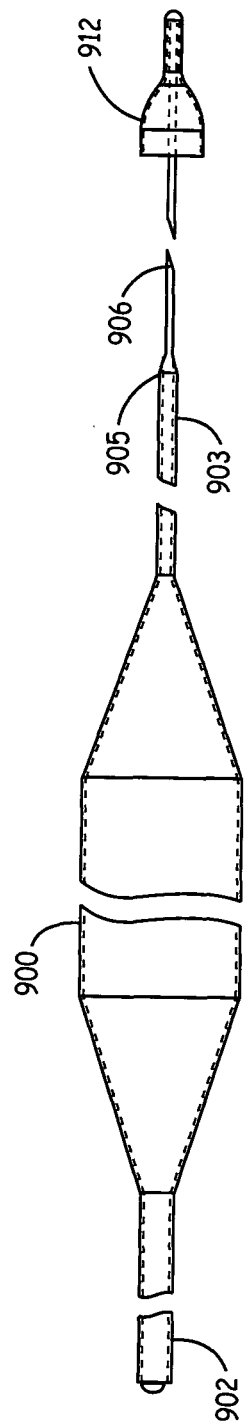

With reference to FIG. 9F, an illustration of a flow delivered tethered balloon for use in harvesting a vessel section in one embodiment of the present invention is shown. This embodiment utilizes a tether 906 coupled to the routing neck 903 to introduce a balloon 900 into a vessel section, e.g., a saphenous vein, during a vessel harvesting procedure. Balloon catheter 900 is sealed at its proximal end 902. In one embodiment, the distal end 905 of balloon catheter 900 is attached or bonded to the proximal end of tether 906. In one embodiment, routing neck 903 of balloon catheter 900 may be approximately 200 mm in length. In one embodiment, tether 906 may be approximately 500 mm in length. Parachute 912, approximately 2-5 mm in diameter, is coupled or attached to the proximal end of tether 906. It is of note that parachute 912 may be a cup shaped component, a lightweight ball, or anything that is easily carried by fluid flow without departing from the spirit of the invention. Tether 906 can be a thin string, such as thread or suture material. It could also be something with more stiffness so that it could be pushed into the vein while injecting fluid.

Figure 11:
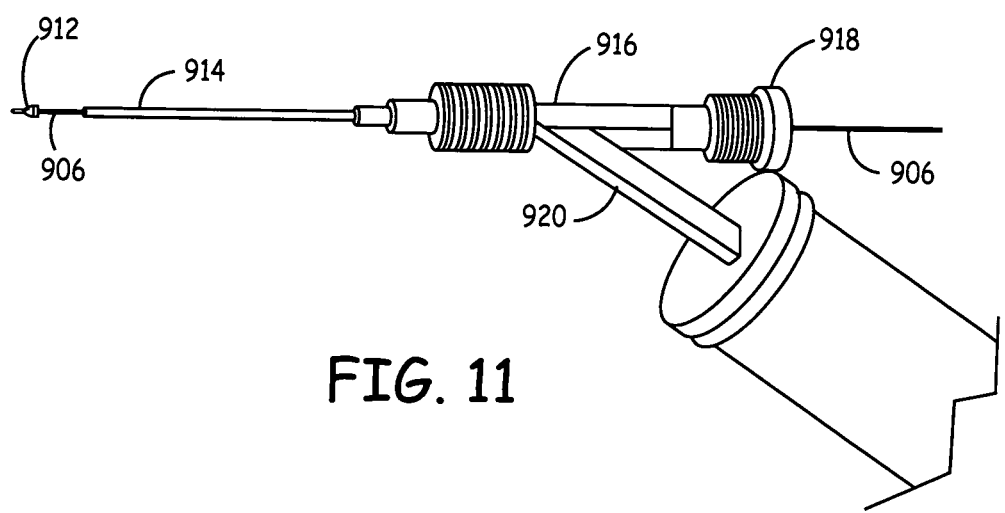
FIG. 11 is an illustration of an insertion device for a flow delivered tethered balloon for use in harvesting a vessel section in an embodiment of the present invention.

With reference to FIG. 11, an illustration of an insertion device for a flow delivered tethered balloon, as shown in FIG. 9F, for use in harvesting a vessel section in one embodiment of the present invention is shown. Tether 906 may be introduced into the vessel through a vessel cannula 914 connected to a y-connector 916 with a Touhy Borst valve 918. Valve 918 can be tightened as much as possible to prevent backflow of fluid, e.g., blood or saline, but still allow tether 906 to move. Port 920 of y-connector 916 is used to inject fluid, e.g., saline. Cannula 914 is inserted into the proximal end of a vessel section to be harvested, e.g., a saphenous vein section, and sutured into position. For a saphenous vein the proximal end of the section to be harvested is located near the knee. The distal end of the vessel, near the groin region, is opened to allow parachute 912 to exit the vessel section to be harvested. Tether 906 is injected into vessel at a location near the knee using fluid, such as saline, to carry parachute 912 from the knee to the groin incision. Balloon 900 is then pulled into position within the vessel at a desired location. After balloon 900 is inflated, the cutting device is inserted at the knee incision to perform the harvest. The fluid used to advance parachute 912 may be saline, blood, heparanized saline, or any other biocompatible fluid without departing from the spirit of the invention. In one embodiment, one or more fluids may be injected through port 920 to flush the vessel before, during and/or after insertion of balloon 900. In one embodiment, parachute 912 allows balloon 900 to be pulled into the vessel by tether 906, rather than pushed into the vessel with a stylet, for example.

With reference to FIGS. 12A-12F illustrations of vessel support devices for use in harvesting a vessel section in one embodiment of the present invention are shown. The following discussion involves alternatives to using the balloon concepts discussed in detail above for vessel support. Specifically ways to provide stabilization or support to a vessel during a harvesting procedure by placing a support member inside the vessel. Theses alternatives include inserting a rod or dilator into a flexible sheath or coiled tube, using a wire braid that increases in diameter when compressed, a tapered rod or dilator, a rod or dilator with a flexible tip, a tube or dilator having irrigation holes, and a rod or dilator with slippery, lubricious coating, e.g., an Advawax coating or a hydrogel coating. Other lubricious coatings, as discussed above, may be used. These varied concepts all provide a support structure that is placed within the vessel section that is to be harvested, thereby providing the harvesting tool a structure to follow, while preserving the endothelial lining of the vessel. Some of the concepts provide for a small diameter during insertion and removal and a larger diameter during the cutting procedure. Some embodiments create a fluid barrier between the support member and the vessel wall.

Inserting a rod or dilator into a flexible sheath or coiled tube may be used to expand the flexible sheath or coiled tube. The flexible sheath or coiled tube may be inserted into the vessel with a smaller diameter, then expanded to a larger diameter with the rod or dilator, thereby achieving the desired diameter and stiffness. The rod or dilator may then be removed from the flexible sheath or coiled tube when it is desirable to have a smaller diameter to remove the flexible sheath or coiled tube from the vessel. The flexible sheath may be an elastomeric tube, approximately the length of the vessel section to be harvested. The flexible sheath would be capable of expanding to the desired diameter when a rod or dilator is inserted. Since the rod or dilator would be slid into the flexible sheath or coiled tube, rod or dilator and sheath materials that create minimal friction would be desirable. The coiled tube may be a piece of thin-walled, coiled polymer, such as Teflon, that had a heat set in the coiled configuration. The coil would unwind as the dilator is inserted, thereby expanding to the desired diameter.

Figure 12A:
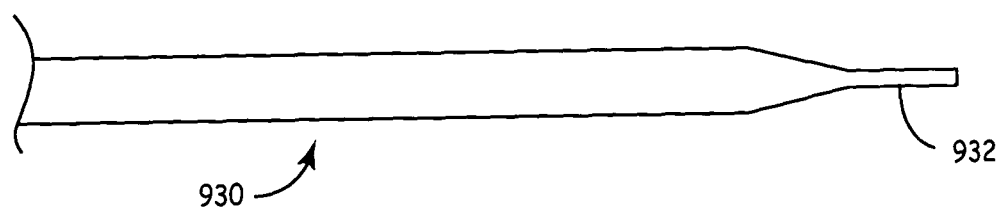
FIGS. 12A-12C shows illustrations of vessel support devices for use in harvesting a vessel section in an embodiment of the present invention.

FIG. 12A shows one embodiment of a dilator 930 that could be placed within the vessel to be harvested. Dilator 930 has a flexible tip 932 which is much more narrower than the diameter of dilator 930, e.g., approximately 5 mm. Tip 932 may extend roughly 1 cm from the main body of dilator 930 and provides a guide for insertion of dilator 930 into a vessel section to be harvested. Dilator 930 may be made of a Teflon material so it would slide more easily though the vessel, thereby helping preserve the endothelial lining of the vessel. In one embodiment, dilator 930 may be inserted through a cannula 914 having diameter large enough to allow dilator 930 to pass through. One or more fluids as discussed above may be injected through port 920 to irrigate the vessel before, during and/or after insertion of dilator 930.

Figure 12B:
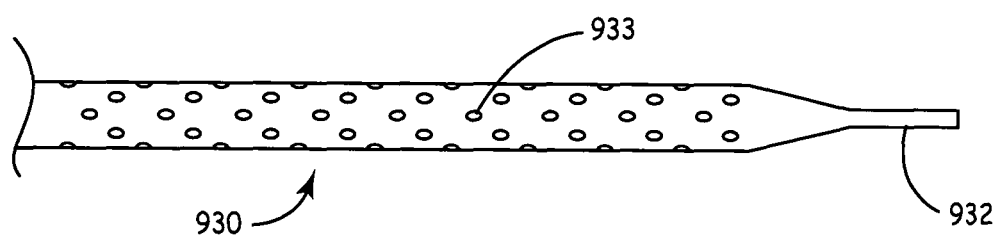

FIG. 12B shows one embodiment of dilator 930 having one or more holes 933. Holes 933 allow the user to inject one or more fluids, e.g., saline, through the dilator to create pressure in the vessel thus expanding it outward and making the insertion of the dilator easier. The injection of fluid can creates a fluid barrier between the dilator and the vessel wall to minimize endothelial damage.

Figure 12C:
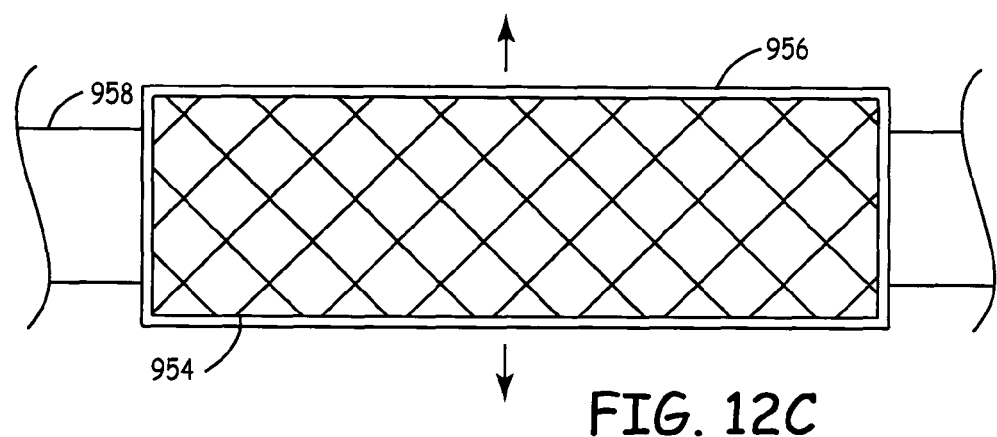

The end of the vessel may be tied off to retain the added fluid(s), such as saline. Fluid may be added to the vessel to achieve an internal vessel pressure of roughly 50-200 mmHg during insertion and removal of dilator 930. In one embodiment, fluid(s) containing one or more medical, biological and/or pharmaceutical agents and/or drugs may be delivered to the vessel before, during and/or after a vessel harvesting procedure. One or more fluids may be delivered via one or more fluid delivery devices, e.g., a syringe or a pressurized fluid reservoir. The vessel may be secured by tying the vessel around features protruding from the side of the dilator. In one embodiment, a needle 948, for example, may be inserted into the vessel section to be harvested. The needle is then used to fill the vessel section with fluid(s) before, during and/or after insertion of dilator 930. In one embodiment, a small pressure relief hole may be created in the vessel section to insure the vessel is not damaged due to a large internal fluid pressure during the harvesting procedure. In one embodiment, a pressure gauge may be used to accurately monitor the internal pressure of the fluid filled vessel section. FIG. 12C shows a vessel support device 954 comprising a braided cylindrical structure similar to a vascular stent. In one embodiment, a flexible protective membrane 956 is placed over device 954 to protect the endothelial layer by shielding the vessel wall from the wire braid during insertion and removal of device 954 during a vessel harvesting procedure. After support device 954 is inserted into the vessel, one end of device 954 is then fixed to the vessel. An insertion tool 958 is inserted within device 954 to cause device 954 to expand to the diameter of the vessel.

Figure 13A:
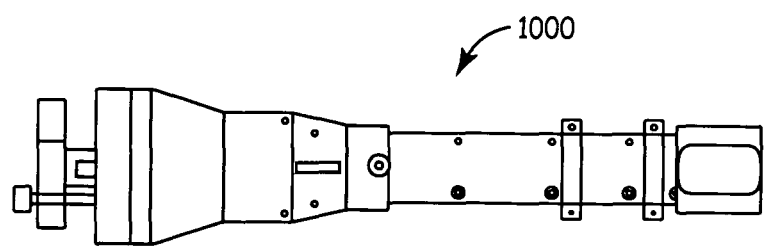
FIGS. 13A-13F are illustrations of handle embodiments with a vessel tensioning device for use in harvesting a vessel section in an embodiment of the present invention.
Figure 13B:
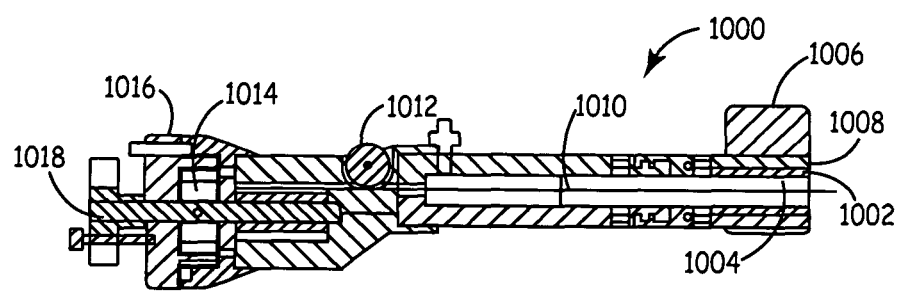
Figure 13C:
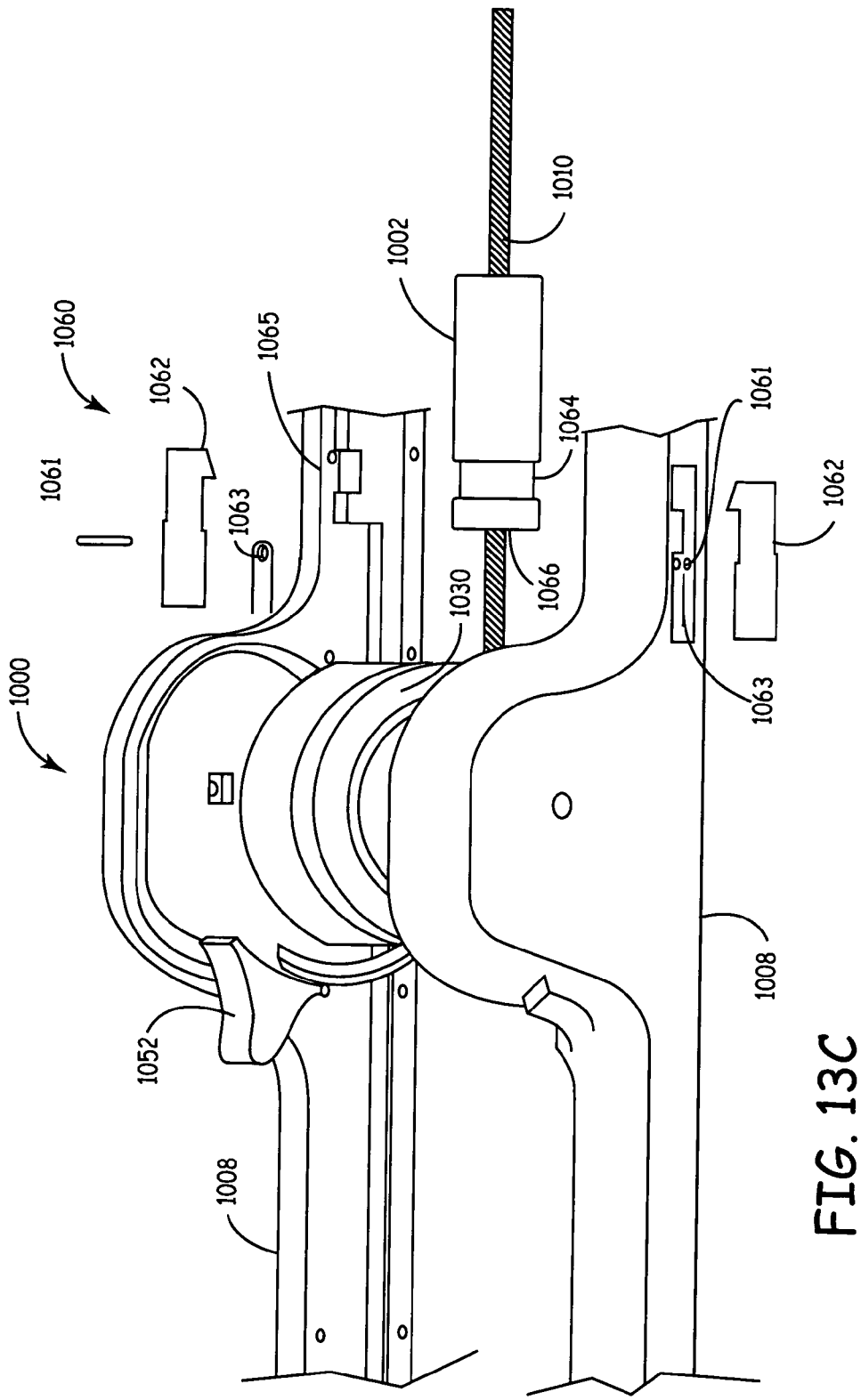
Figure 13D:
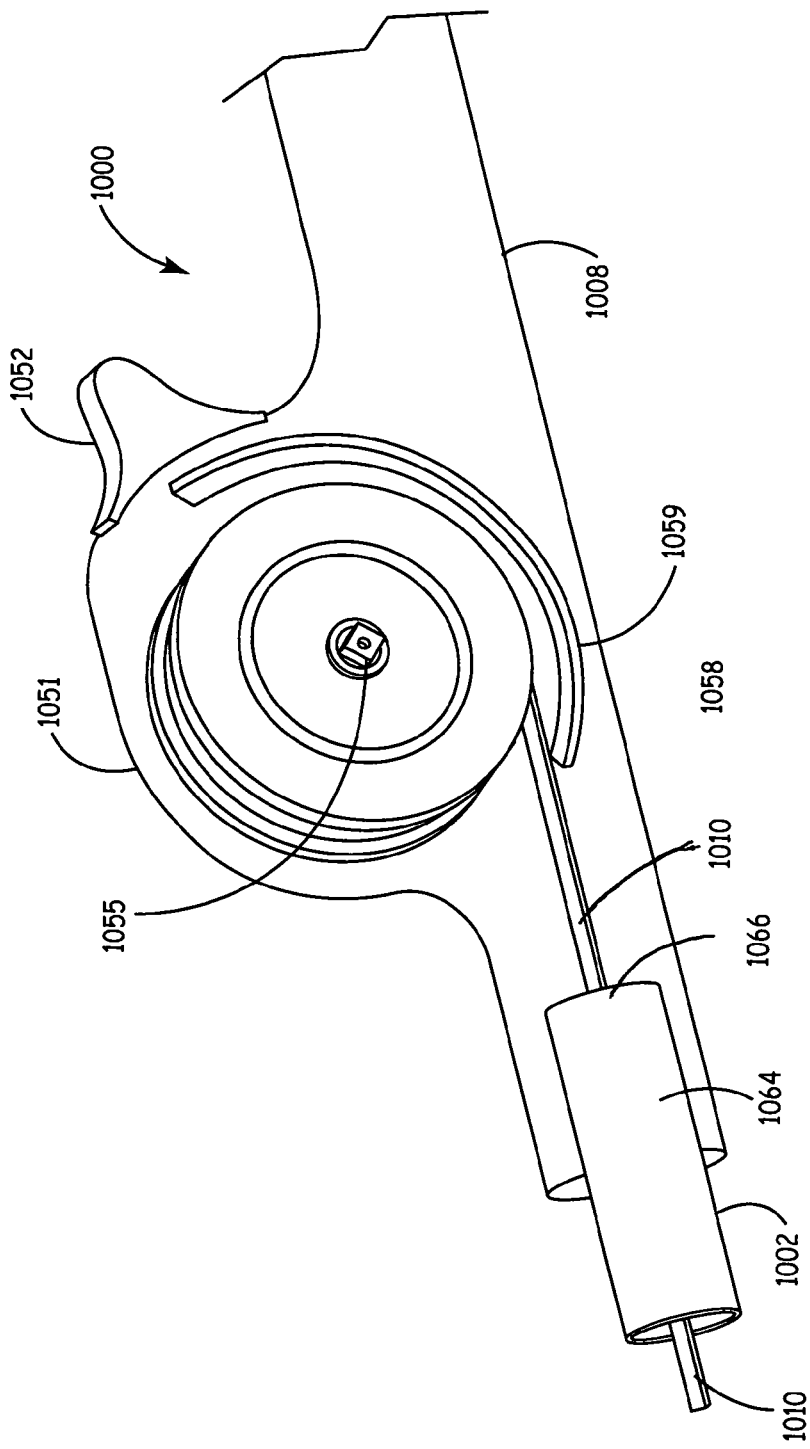
Figure 13E:
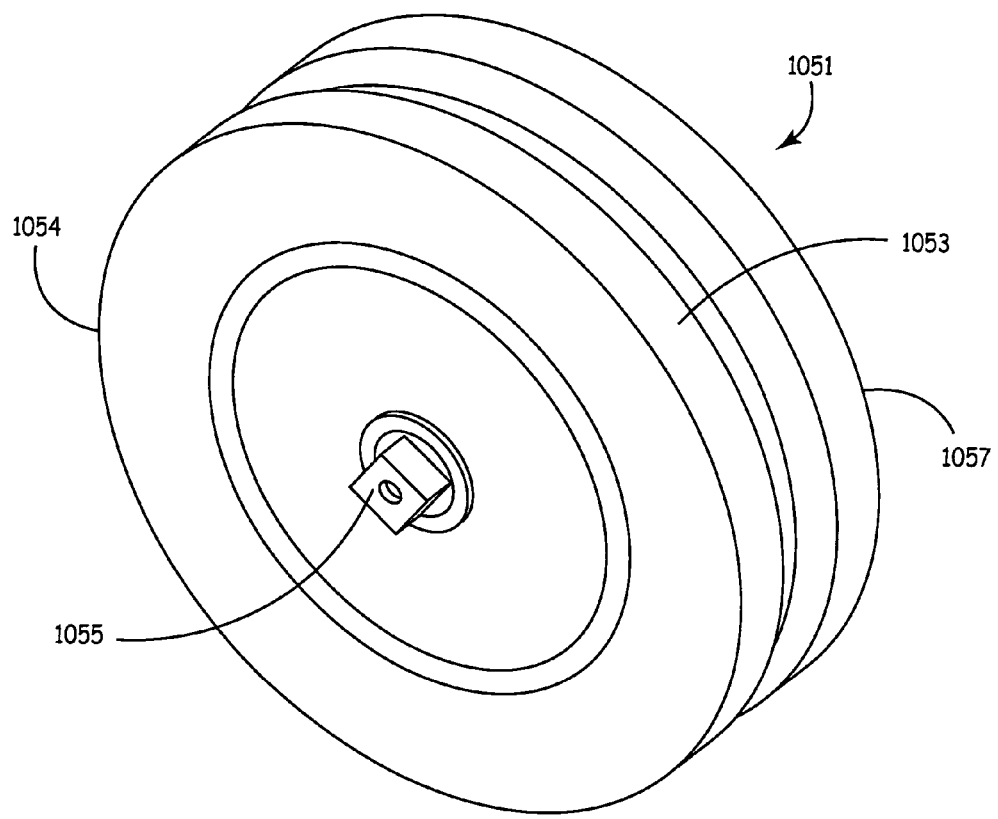
Figure 13F:
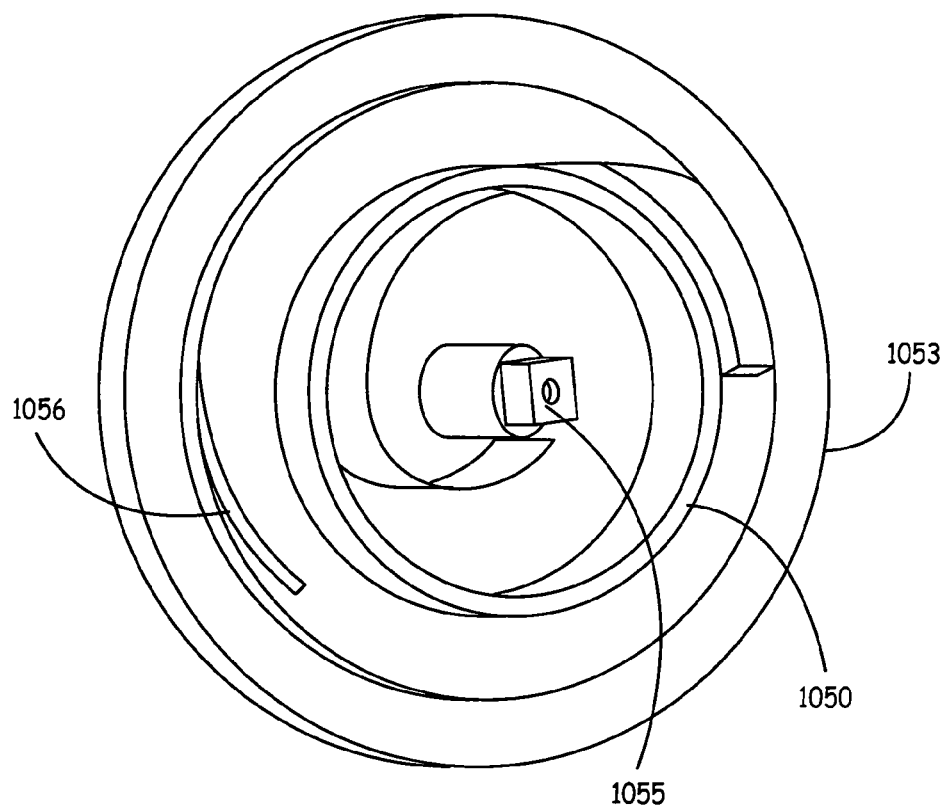

With respect to FIGS. 13A-13B, an illustration of one embodiment of a handle including a vessel-tensioning device for use in harvesting a vessel section in an embodiment of the present invention is shown. Handle 1000 is comprised of outer tubular member 1002, inner vein stabilizer tube 1004, outer knife blade turning collar 1006, handle body 1008, vein tensioning cable 1010, tensioning cable clamping wheel 1012, tensioning spring 1014, spring tensioning adjuster 1016, and tensioning control knob 1018. In one embodiment, the distal end of tensioning cable 1010 may be coupled to the proximal end 863 of vessel-tensioning device member 861. The vessel-tensioning device may supply a predetermined amount of pressure, e.g., 12 oz, on the cannula 851 and vessel. This pressure on the cannula and vessel is used to hold the vessel section to be harvested in its original starting position.

With respect to FIGS. 13C-13F, an illustration of one embodiment of a handle including a vessel-tensioning device for use in harvesting a vessel section in an embodiment of the present invention is shown. Handle 1000 is capable of coupling the proximal end of cutting tubular member 1002, handle body 1008, vein tensioning cable or tape 1010, spring bobbin assembly 1051, vein tensioning brake 1052, and cutting tubular member locking assembly 1060. In one embodiment, the distal end of tensioning cable 1010 may be coupled to the proximal end 863 of vessel-tensioning device member 861. The vessel-tensioning device may supply a predetermined amount of pressure, e.g., 12 oz, on the cannula 851 and vessel. This pressure on the cannula and vessel is used to hold the vessel section to be harvested in its original starting position.

In one embodiment, bobbin assembly 1051 includes tensioning bobbin spring 1050, bobbin members 1053 and 1054, and bobbin shaft 1055. Bobbin shaft 1055 couples bobbin assembly 1051 to handle body 1008. The proximal end of tensioning cable or tape 1010 is fixed attached to bobbin assembly 1051 via placement with slot 1056. Tensioning cable or tape 1010 is wound around bobbin assembly 1051 within recess 1057. Bobbin spring 1050 supplies the tensioning force to the cable or tape 1010. The distal end 1059 of tensioning brake 1052 applies a variable force against tensioning cable or tape 1010. The force applied by brake 1052 pushes tape 1010 against and into notches or grooves 1058. Pressing down on the proximal portion of brake 1052 translates into a greater force being applied to tape 1010 via the distal portion of brake 1052.

In one embodiment, cutting tubular member locking assembly 1060 includes two pins 1061, two locking members 1062, and two springs 1063. Locking members 1063 and springs 1062 are coupled to handle body members 1008 via pins 1061. Springs 1062 bias locking members 1063 into a locking position with the proximal end of cutting tubular member 1002. Portions of locking members 1062 fit into recess 1064 located at the proximal end of cutting tubular member 1002. The proximal end of cutting tubular member 1002 also comprises slots 1066. Raised portions 1065 of handle body members 1008 fit into slots 1066, thereby preventing the rotation of cutting tubular member 1002 in relation to handle body 1008. Rotation of handle body 1008 will translate to a rotation of cutting tubular member 1002.

It is very helpful to keep the vessel taught to not allow the vessel to start to migrate forward with the handle as this subjects the vessel to bunch, which can lead to cutting the main portion of the vessel. The tensioning system is used to hold the vessel in position while the cutting tool is advanced over the vessel. In one embodiment, the tensioning system may improve the quality of the harvested vessel.

Figure 14A:
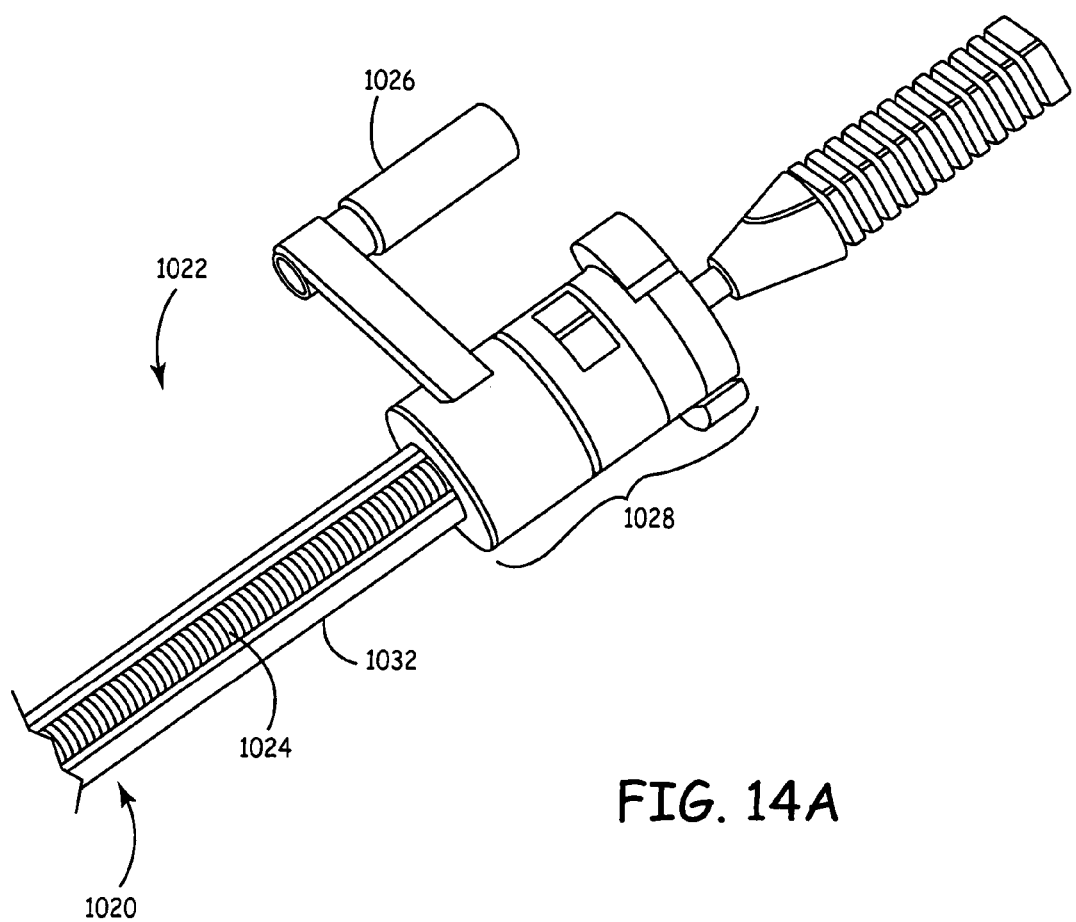
Figure 14C:
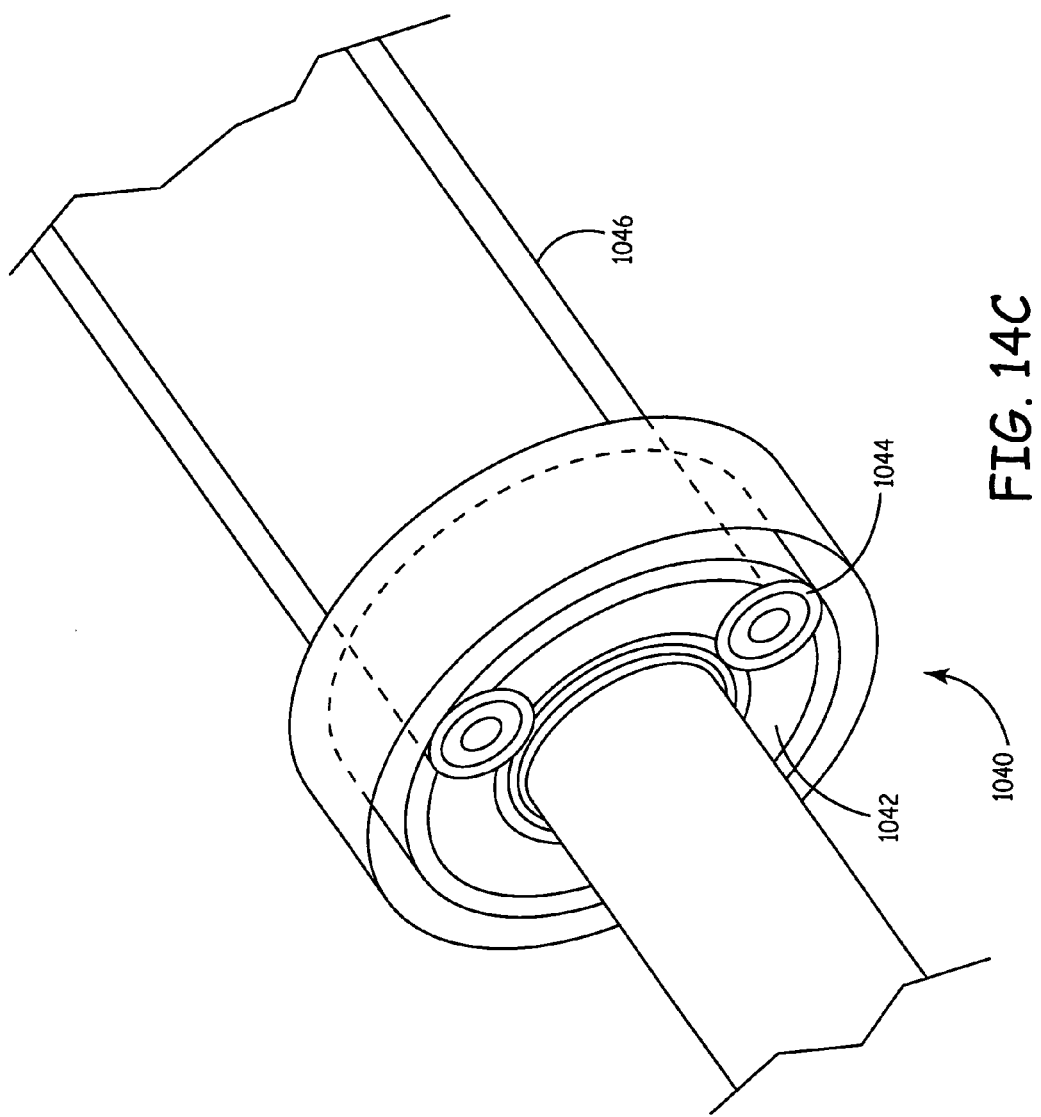

With reference to FIGS. 14A-C, illustrations of one embodiment of a drive system for use in harvesting vessel sections in some embodiments of the present invention is shown. The figures show a system intended to amplify user input (rotation) to the main body 1020 of device 1022 and another that is intended to assist advancement of device 1022 given user input. The figures shown for amplifying user input is based on a planetary gear arrangement that provides angular increase of approximately double the input. Altering gear systems 1028 can attain other input/output ratios. The drive system design to provide device advancement utilizes a ratcheting mechanism on a lead screw 1024 to move the cutting edge forward. With the ratcheting feature the device is advanced during the clockwise rotation of grip 1026. Counter-clockwise rotation provides a secondary cutting stroke and resets the ratchet mechanism for the next advancing stroke.

FIG. 14B shows drive and release system 1030 for cutting tubular member 1032. In system 1030, push buttons 1034 must be pressed together by the operator to release nut 1038 from thread 1024 for free movement of cutting tubular member 1032 along thread 1024. It is of note that the vessel stabilization channel traverses through the threaded section. Clockwise rotation advances system 1030 along threaded member 1024. The pitch of the thread and angle of rotation determines the travel distance. Counter clockwise rotation resets pawls 1036 on nut 1038 to prepare for the next advance. Counter clockwise rotation also provides a second swipe of the cutting device across tissue before the next advance. It is of note that pawls 1036 are spring loaded against nut 1038. It is also of note that pawls 1036 can be disengaged for manual operation. FIG. 14C shows planetary gear system 1040 having a pinion gear 1042 and ring gears 1044. Planetary gear 1040 is located at the end of handle 1046.

Figure 15:
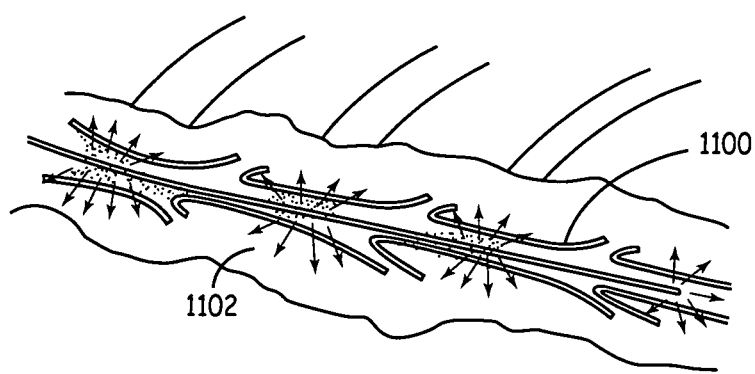
FIG. 15 is an illustration of a vein illumination device for use in harvesting vessel sections in an embodiment of the present invention.

With reference to FIG. 15, an illustration of a vein illumination device for use in harvesting vessel sections in one embodiment of the present invention is shown. As discussed, current vessel harvesting is a tedious, labor-intensive process. Harvesting is often accomplished with an electrosurgical tool to cut away tissues around the vessel to be harvested so as to free the vessel, e.g., from the leg, the chest wall or other body structure. In some harvesting procedures, the location of the vessel has to be repeatedly assessed and verified by the surgeon to be sure to stay clear of the vessel with the surgical tool to avoid damaging the vessel. To prevent bleeding from the vessel or vessel attachment points, side branches of the vessel may be occluded, for example, via clips, sutures, or electrocautery. Therefore, one embodiment of the present invention discloses illuminating the vessel from the inside out to make the location of the vessel readily visible in order to cut around it. Another embodiment involves a catheter like device within the vessel to act as a guide for an external cutter to harvest the vessel away from the native tissue. A further embodiment, controls bleeding from the vessel side branches by dispensing into the side branches a material that occludes and plugs the side branch allowing the branch to be cut without applying clips, sutures, or electrocautery.

FIG. 15 shows illuminating a vessel 1100 with an intravenous catheter device emitting light 1102, e.g., via fiber optics. This illumination is designed to aid visualization of the vessel, e.g., the internal mammary artery (IMA), radial artery, saphenous vein or similar vasculature during cut down to aid in the vessel harvesting procedure.

Figure 16:
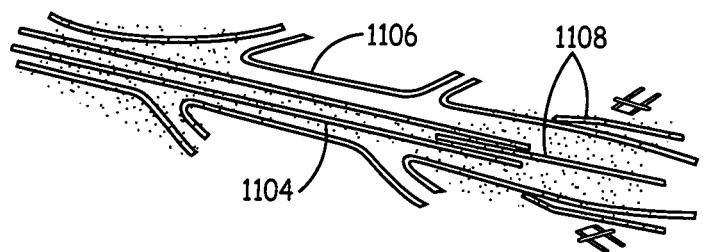
FIG. 16 is an illustration of a catheter guide for use in harvesting vessel sections in an embodiment of the present invention.

FIG. 16 shows an intravenous catheter device 1104 placed within a vessel 1106 to serve as a centering guide for advancing a vessel-cutting device 1108 along the exterior of vessel 1106.

Figure 17:
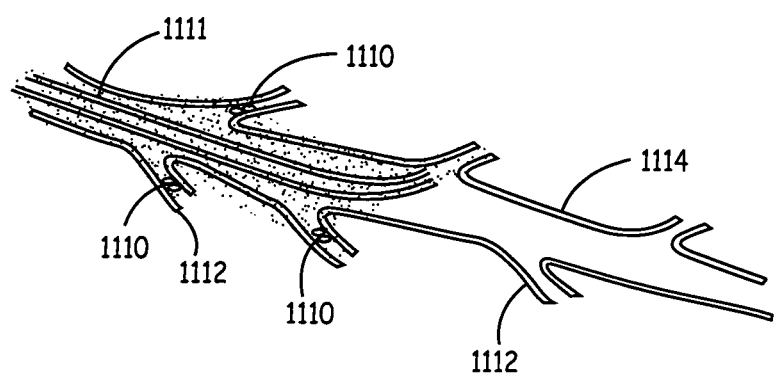
FIG. 17 is an illustration of hemostatic control device for use in harvesting vessel sections in an embodiment of the present invention.

With respect to FIG. 17, an illustration of a hemostatic control device 1111 for use in harvesting vessel sections in one embodiment of the present invention is shown. Hemostatic material 1110 is shown deployed from the hemostatic control device 1111 positioned within the vessel section to be harvested. In one embodiment, vessel side branches 1112 of the vessel section to be harvested may be occluded or plugged prior to the vessel harvesting procedure. Hemostatic material 1110 can maintain hemostasis without the time consuming process of ligating or cauterizing each branch during a vessel harvesting procedure. Hemostatic material 1110 may be made of UV curable glue or adhesive, a platelet gel material, an expanding hydrogel material, and/or other biocompatible hemostatic material.

Figure 18:
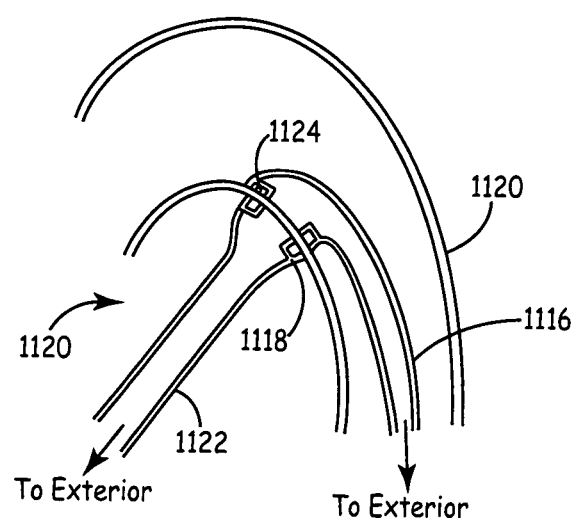
FIG. 18 is an illustration of a vessel location and hemostasis device for use in harvesting vessel sections in an embodiment of the present invention.

With reference to FIG. 18, an illustration of a vessel location and hemostasis device for use in harvesting vessel sections in one embodiment of the present invention is shown. In operation, a hollow guide 1122 is inserted through the chest wall, for example. A distal end of hollow guide 1116 has a ring/oval magnet 1118 attached. The distal end is placed against vessel exterior 1120 at a target anastomosis location. Hollow guide 1116 is then placed into vessel 1120, e.g., an IMA vessel. Intravascular guide 1116 has a ring/oval magnet 1124 attached at its distal end. Intravascular guide is magnetically attracted to extravascular hollow guide 1122 trapping the vessel wall between them. Once the vessel wall between the two guides is penetrated, the rings form a hemostatic seal and hollow guides 1116 and 1122 now form a continuous channel to pass guidewires, catheters, hemostatic control devices through the vessel wall.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

What is claimed is:

1. A cutting device for harvesting a vessel section, comprising:
    an outer tubular member having at least one cutting element positioned adjacent to a distal end of the outer tubular member;
    an inner tubular member slidably received within a lumen of the outer tubular member, wherein the outer and inner tubular members are capable of being advanced over a vessel section to core out the vessel section and tissue adjoining the vessel section;
    a rollout intravascular sheath to protect the vessel's endothelial layer during insertion of a vessel support device, wherein the sheath terminates at opposing, first and second ends; and
    an inner tube that rolls out the rollout sheath as the inner tube is advanced into the vessel, the inner tube defining an outer surface, an inner passageway, a leading end and a trailing end;
    wherein the first end of the sheath is slidably coupled to the outer surface, an intermediate section of the sheath is inverted about and abuttingly contacts the leading end and the opposing second end of the sheath projects from the inner passageway and beyond the trailing end such that as the first end of the sheath is held stationary and the inner tube is longitudinally advanced relative to the first end, the sheath unrolls.

2. The device of claim 1, wherein the rollout sheath is a flexible tube.

3. The device of claim 1, wherein the vessel support device is an inflatable vessel support member.

4. The device of claim 1, further comprising means for providing hemostatic control of branch vessels severed by the cutting element as the outer tubular member is advanced over the vessel section.

5. The device of claim 4, wherein the hemostatic control means comprises a biological sealant.

6. The device of claim 5, wherein the biological sealant comprises a platelet gel.

7. The device of claim 1, wherein the outer tubular member and the inner tubular member are co-axially arranged relative to one another.

8. The device of claim 1, wherein the rollout intravascular sheath comprises a material body terminating at the opposing, first and second ends, and further wherein the rollout intravascular sheath is configured to transition from an initial state to a deployed state by longitudinal movement of the first end relative to the second end.

* * * * *